United States Patent
Guirakhoo et al.

(10) Patent No.: US 11,801,299 B2
(45) Date of Patent: Oct. 31, 2023

(54) COMPOSITIONS AND METHODS FOR GENERATING AN IMMUNE RESPONSE TO HEPATITIS B VIRUS

(71) Applicant: Georgia State University Research Foundation Inc., Atlanta, GA (US)

(72) Inventors: Farshad Guirakhoo, Atlanta, GA (US); Arban Domi, Atlanta, GA (US); Nathanael P. McCurley, Decatur, GA (US); Rahul Basu, Atlanta, GA (US); Ming Luo, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 26 days.

(21) Appl. No.: 17/368,761

(22) Filed: Jul. 6, 2021

(65) Prior Publication Data
US 2022/0118082 A1    Apr. 21, 2022

Related U.S. Application Data

(63) Continuation of application No. 16/305,305, filed as application No. PCT/US2017/034983 on May 30, 2017, now Pat. No. 11,052,148.

(60) Provisional application No. 62/343,074, filed on May 30, 2016.

(51) Int. Cl.
| | |
|---|---|
| *A61K 39/29* | (2006.01) |
| *A61P 31/14* | (2006.01) |
| *A61K 39/12* | (2006.01) |
| *A61K 39/295* | (2006.01) |
| *A61K 9/00* | (2006.01) |
| *A61K 39/00* | (2006.01) |

(52) U.S. Cl.
CPC ............... *A61K 39/29* (2013.01); *A61K 9/006* (2013.01); *A61K 9/0019* (2013.01); *A61K 39/12* (2013.01); *A61P 31/14* (2018.01); *A61K 39/295* (2013.01); *A61K 2039/57* (2013.01); *C12N 2710/24143* (2013.01); *C12N 2730/10123* (2013.01); *C12N 2730/10134* (2013.01)

(58) Field of Classification Search
None
See application file for complete search history.

(56) References Cited

U.S. PATENT DOCUMENTS

| | | |
|---|---|---|
| 9,133,480 B2 | 9/2015 | Moss et al. |
| 2010/0316989 A1 | 12/2010 | Jeon et al. |
| 2012/0263750 A1 | 10/2012 | Moss et al. |
| 2013/0011435 A1 | 1/2013 | Martin et al. |
| 2019/0030158 A1 | 1/2019 | Protzer et al. |

FOREIGN PATENT DOCUMENTS

WO    WO 2011/047031 A1    4/2011

OTHER PUBLICATIONS

U.S. Pat. No. 11,052,148, A1, U.S. Appl. No. 16/305,305, Guirakhoo et al., Jul. 6, 2021.
Cai Xiaodan et al: "A virus-like particle of the hepatitis B virus pres antigen elicits robust neutralizing antibodies and T cell responses in mice", Antiviral Research, vol. 149, Jan. 1, 2018 (Jan. 1, 2018), pp. 48-57.
Cavenaugh, JS et al., Partially Randomized, Non-Blinded Trial of DNA and MVA Therapeutic 4, 17,22,23 Vaccines Based on Hepatitis B Vims Surface Protein for Chronic HBV Infection. Plos ONE. Feb. 15, 2011. vol. 6, Issue 2.
Ciupe, SM et al., Antibody Responses during Hepatitis B Viral Infection. Plos ONE. Jul. 31, 2014. vol. 10, Issue 7.
Davenport, MP et al., Kinetics of Virus-Specific CD8+ T Cells and the Control of Human Immuno-deficiency Virus Infection. Journal of Virology, Sep. 2004, vol. 78, No. 18, pp. 10096-10103.
Extended European Search Report from EP Patent Application No. 17807327.6, dated Jan. 17, 2020.
Franco, E. et al., Hepatitis B: Epidemiology and prevention in developing countries. World Journal of Hepatology. Mar. 27, 2012. vol. 4, No. 3pp. 74-80.
Hartmann-Stuhler, C. et al., Hepatitis B Virus Large Envelope Protein Interacts with (gamma]2-Adaptin, a Clathrin Adaptor-Related Protein. Journal of Virology. Jun. 2011. vol. 75, No. 11, pp. 5343-5351.
Holmes, Ket al., Assembly Pathway of Hepatitis B Core Vims-like Particles from Genetically 13 Fused Dimers. The Journal of Biological Chemistry, May 7, 2015. vol. 290, No. 26, pp. 16238-16245.
Hung et al. PLoS ONE 6(12):e28977, 2011.
International Search Report from PCT Patent Application No. PCT/US2017/034983 dated Aug. 24, 2017.
Ming Luo: "A virus-like particle of HBV press elicits robust immune responses—5th World Congress on Hepatitis & Liver Diseases 2nd International Conference on Pancreatic Cancer & Liver Diseases", Journal of Liver, vol. 06, Aug. 10, 2017.
Raimondo et al. "Occult HBV infection," Semin Immunopathol, 35:39-52, 2013.
Vietheer et al., "Immunizations with chimeric hepatitis B virus-like particles to induce potential anti-hepatitis C virus neutralizing antibodies," Antiviral Therapy, 12:477-487, 2007.
Walsh, R. et al., Hepatitis B Precore Protein: Pathogenic Potential and Therapeutic Promise. Yonsei Medical Journal. 2012. vol. 53, No. 5, pp. 875-885.

(Continued)

*Primary Examiner* — Nicole Kinsey White
(74) *Attorney, Agent, or Firm* — Knowles Intellectual Property Strategies, LLC

(57) ABSTRACT

The compositions and methods are described for generating an immune response to a hepatitis B virus. The compositions and methods described herein relate to a modified vaccinia Ankara (MVA) vector encoding one or more viral antigens for generating a protective immune response to a hepatitis B virus, in the subject to which the vector is administered. The compositions and methods of the present invention are useful both prophylactically and therapeutically and may be used to prevent and/or treat an infection caused by hepatitis B virus.

15 Claims, 4 Drawing Sheets

Specification includes a Sequence Listing.

(56) References Cited

OTHER PUBLICATIONS

Wyatt et al., "Elucidating and Minimizing the Loss by Recombinant Vaccinia Virus of Human Immunodeficiency Virus Gene Expression Resulting from Spontaneous Mutations and Positive Selection," Journal of Virology, 83(14):7176-7184, 2009.

Zhao, Z et al., Mucroporin-M1 Inhibits Hepatitis B Virus Replication by Activating the Mitogen-activated Protein Kinase (MAPK) Pathway and Down-regulating HNF4[alpha] in Vitro and in Vivo. The Journal of Biological Chemistry. Aug. 3, 31, 2012, vol. 287, No. 36, pp. 30181-30190.

Soulie, J.C. et al. Immunogenicity and safety in newborns of a new recombinant hepatitis B vaccine containing the S and pre-S2 antigens, Vaccine, vol. Aug. 9, 1991, 545-548.

Valenzuela, Pablo, et al. Synthesis and assembly of hepatitis B virus surface antigen particles in yeast, Nature vol. 298 Jul. 22, 1982.

SEQUENCE LISTING

```
<160> NUMBER OF SEQ ID NOS: 8

<210> SEQ ID NO 1
<211> LENGTH: 849
<212> TYPE: DNA
<213> ORGANISM: Hepatitis B Virus

<400> SEQUENCE: 1
atgcaatgga attctacaac atttcatcaa acactacaag atccaagagt tagaggacta      60
tacttcccag cgggtggaag ttcttctggt gctgtaaatc cagtaccaac aacagcgagt     120
ccactatctt ctattttctc tagaattgga gatccagcgc taaatatgga gaatattaca     180
tctggatttc taggaccact actagtacta caagcgggat tcttcctact aacaagaatt     240
ctaacaattc cacaatctct agattcttgg tggacatctt tgaatttcct gggaggaaca     300
acagtatgtc taggacagaa ttctcaatct ccaacatcta atcattctcc aacaagttgt     360
ccacctacat gtccaggata tagatggatg tgtctaagaa gattcattat cttcttgttc     420
attctactac tatgtctaat tttcctattg gtactactag attatcaagg aatgctacca     480
gtatgtccat tgattccagg atcttctaca acttctacag gaccatgtag aacttgtatg     540
acaacagcgc aaggtactag tatgtatcca tcttgttgtt gtacaaagcc atctgatgga     600
aattgtacat gtattccaat tccatcttct tgggcgtttg gaaagtttct atgggaatgg     660
```

```
gcgtctgcga gattctcttg gctatctttg ctagtaccat tgttcaatg gtttgttgga    720 ctatctccaa ctgtatggct atctgtaatt tggatgatgt ggtattgggg accatctcta    780
tattctattc tatctccatt tctaccacta ttgccaatct tcttctgtct atgggtatac    840
atataataa                                                             849

<210> SEQ ID NO 2
<211> LENGTH: 639
<212> TYPE: DNA
<213> ORGANISM: Hepatitis B virus

<400> SEQUENCE: 2
atgcatctat tcatctatg tttgattatt tcttgttctt gtccaacagt acaagcgtct     60
aaactatgtc taggatggct atggggaatg gatattgatc cttataaaga atttggagcg    120
acagtagaac tactatcttt cctaccatct gatttcttcc catctgttag agatctacta    180
gatacagcgt ctgcgttgta tagagaagcg ctagaatctc cagaacattg ttctccacat    240
catacagcgc taagacaagc gattctatgt tggggagaac taatgacact agcgacatgg    300
gttggagtaa atctagaaga tccagcgtct agagatttgg tagtatctta tgtaaataca    360
aatatgggat tgaagtttag acaactacta tggtttcata tatcttgtct aacatttgga    420
agagaaacag taattgaata tctagtatct ttcggagtat ggattagaac caccaccagcg    480 tatagaccac caaatgcgcc aattctatct acactaccag aaacaacagt agttagaaga    540
agaggaagat ctccaagaag aagaacacca agtcctagaa gaagaagatc acaatcacca    600
agaagaagaa gaagtcaatc tagagaacca caatgttaa                           639

<210> SEQ ID NO 3
<211> LENGTH: 342
<212> TYPE: DNA
<213> ORGANISM: Hepatitis B virus

<400> SEQUENCE: 3
atggctgcga gactatgttg tcaactagat ccagcgagag atgtactatg tctaagacca     60
gttggagcgg aatcttgtgg tagaccattc tctggatctc tagaaacact atcttctcca    120
tctccatctg cggttccaac agatcatggt gctcatctat ctctaagagg actaccagct    180
atgtctacaa cagatctaga agcttacttc aaggattgtt tgttcaaaga ttgggaagaa    240
ttgggagaag aaattagatt gaaagtattc gttctgggag gatgtagaca taaactagtt    300
tgtgcgccag cgccatgtac attctttaca tctgcgtaat aa                       342

<210> SEQ ID NO 4
<211> LENGTH: 691
<212> TYPE: DNA
<213> ORGANISM: Artificial sequence
<220> FEATURE:
<223> OTHER INFORMATION: preS.HA (SHA) is a chimeric protein, including
      the signal peptide of influenza HA, preS, and the
      transmembrane/cytoplasmic domains of influenza HA.

<400> SEQUENCE: 4
atggaagcga agctattcgt cctattctgt gcgttcacag cgctaaaggc tatgggaacg     60
aatctatctg taccgaatcc gctaggattc ttcccagatc atcaactaga tccagcgttt    120
ggagcgaact ctaacaatcc agattgggac ttcaacccga tcaaggatca ttggccagct    180
gcgaatcaag ttggagttgg agctttcgga ccaggattaa caccaccgca tggtggaata    240
```

```
ttaggatggt caccacaagc gcagggaatc ctaacaaccg tatctacaat tccaccaccg    300
gcgtctacca acagacaatc tggtagacaa ccgacaccaa tctctccgcc gctaagagat    360
tctcatccgc aagctatgca gtggaactct acagctttcc atcaggcgct acaagacccg    420
agagttagag gattatatct accggctggt ggatcctctt ccggaactgt aaatccagcg    480
ccgaatatcg cctctcacat ctcttctatc tctgcgagaa cgggagatcc ggtcaccaac    540
aagttagaat ctgtcggagt ccaccagatc ctagcgatct attctaccgt agcgtcctcc    600
ttggtactac tagtatctct gggagcgatc tccttctgga tgtgttccaa cggatctcta    660
cagtgcagaa tctgcatcta ataatttta t                                    691
```

```
<210> SEQ ID NO 5
<211> LENGTH: 770
<212> TYPE: DNA
<213> ORGANISM: Artificial sequence
<220> FEATURE:
<223> OTHER INFORMATION: M1.P41A is a mutated form (P41A) of influenza
      virus matrix protein responsible for virus budding. The mutation
      P41A is known to drive budding more efficiently

<400> SEQUENCE: 5
atgtcactac taaccgaggt agaaacctac gtcctatcga ttattccgtc cggaccattg     60
aaagcggaga tcgctcagag actagaagga gtattcgctg caagaacac cgatctagag    120 gcgctaatgg aatggctcaa gaccagacca atcctatcgc cgctaacgaa gggaatctta    180
ggattcgtat tcacactaac cgtaccgtcc gagagaggac tacagagaag aagattcgtc    240
cagaacgcgc tcaacggcaa cggagatccg aacaacatgg atagagcggt caagctatac    300
aagaagctca agagagagat caccttccac ggagcgaagg aagtctcact atcttactct    360
actggtgcgc tagcatcctg catgggacta atctataaca gaatgggaac cgtaacaacc    420
gaagcggcgt tcggattagt atgtgcgaca tgtgaacaga tcgcggactc tcagcataga    480
tctcatagac agatggcgac cacaacgaac ccactaatca gacacgagaa tagaatggtc    540
ctagcgtcta caacagcgaa ggccatggaa cagatggcag atcttctga caagctgcg    600 gaagctatgg aagtagcctc tcagacaaga cagatggtcc acgccatgag aaccatcgga    660
acacatccat cttctagtgc aggattgaag gacgacctac tagagaacct acaggcgtac    720
cagaagagaa tgggagtcca gatccagaga ttcaagtaat aatttttat               770
```

```
<210> SEQ ID NO 6
<211> LENGTH: 163
<212> TYPE: PRT
<213> ORGANISM: Hepatitis B virus

<400> SEQUENCE: 6

Met Gly Thr Asn Leu Ser Val Pro Asn Pro Leu Gly Phe Phe Pro Asp
1               5                   10                  15

His Gln Leu Asp Pro Ala Phe Gly Ala Asn Ser Asn Asn Pro Asp Trp
            20                  25                  30

Asp Phe Asn Pro Ile Lys Asp His Trp Pro Ala Ala Asn Gln Val Gly
        35                  40                  45

Val Gly Ala Phe Gly Pro Gly Leu Thr Pro Pro His Gly Gly Ile Leu
    50                  55                  60

Gly Trp Ser Pro Gln Ala Gln Gly Ile Leu Thr Thr Val Ser Thr Ile
65                  70                  75                  80

Pro Pro Pro Ala Ser Thr Asn Arg Gln Ser Gly Arg Gln Pro Thr Pro
                85                  90                  95
```

```
Ile Ser Pro Pro Leu Arg Asp Ser His Pro Gln Ala Met Gln Trp Asn
            100                 105                 110

Ser Thr Ala Phe His Gln Ala Leu Gln Asp Pro Arg Val Arg Gly Leu
        115                 120                 125

Tyr Leu Pro Ala Gly Gly Ser Ser Ser Gly Thr Val Asn Pro Ala Pro
    130                 135                 140

Asn Ile Ala Ser His Ile Ser Ser Ile Ser Ala Arg Thr Gly Asp Pro
145                 150                 155                 160

Val Thr Asn

<210> SEQ ID NO 7
<211> LENGTH: 226
<212> TYPE: PRT
<213> ORGANISM: Artificial sequence
<220> FEATURE:
<223> OTHER INFORMATION: preS.HA (SHA) is a chimeric protein, including
      the signal peptide of influenza HA, preS, and the
      transmembrane/cytoplasmic domains of influenza HA.

<400> SEQUENCE: 7

Met Glu Ala Lys Leu Phe Val Leu Phe Cys Ala Phe Thr Ala Leu Lys
1               5                   10                  15

Ala Met Gly Thr Asn Leu Ser Val Pro Asn Pro Leu Gly Phe Phe Pro
            20                  25                  30

Asp His Gln Leu Asp Pro Ala Phe Gly Ala Asn Ser Asn Asn Pro Asp
        35                  40                  45

Trp Asp Phe Asn Pro Ile Lys Asp His Trp Pro Ala Ala Asn Gln Val
50                  55                  60

Gly Val Gly Ala Phe Gly Pro Gly Leu Thr Pro Pro His Gly Gly Ile
65                  70                  75                  80

Leu Gly Trp Ser Pro Gln Ala Gln Gly Ile Leu Thr Thr Val Ser Thr
            85                  90                  95

Ile Pro Pro Pro Ala Ser Thr Asn Arg Gln Ser Gly Arg Gln Pro Thr
            100                 105                 110

Pro Ile Ser Pro Pro Leu Arg Asp Ser His Pro Gln Ala Met Gln Trp
        115                 120                 125

Asn Ser Thr Ala Phe His Gln Ala Leu Gln Asp Pro Arg Val Arg Gly
    130                 135                 140

Leu Tyr Leu Pro Ala Gly Gly Ser Ser Ser Gly Thr Val Asn Pro Ala
145                 150                 155                 160

Pro Asn Ile Ala Ser His Leu Ser Ser Ile Ser Ala Arg Thr Gly Asp
                165                 170                 175

Pro Val Thr Asn Lys Leu Glu Ser Val Gly Val His Gln Ile Leu Ala
            180                 185                 190

Ile Tyr Ser Thr Val Ala Ser Ser Leu Val Leu Leu Val Ser Leu Gly
        195                 200                 205

Ala Ile Ser Phe Trp Met Cys Ser Asn Gly Ser Leu Gln Cys Arg Ile
    210                 215                 220

Cys Ile
225

<210> SEQ ID NO 8
<211> LENGTH: 252
<212> TYPE: PRT
<213> ORGANISM: Artificial sequence
<220> FEATURE:
<223> OTHER INFORMATION: M1.P41A is a mutated form (P41A) of influenza
```

-continued

```
virus matrix protein responsible for virus budding. The mutation
P41A is known to drive budding more efficiently

<400> SEQUENCE: 8

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Gly Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
            115                 120                 125

Gly Leu Ile Tyr Asn Arg Met Gly Thr Val Thr Thr Glu Ala Ala Phe
        130                 135                 140

Gly Leu Val Cys Ala Thr Cys Glu Gln Ile Ala Asp Ser Gln His Arg
145                 150                 155                 160

Ser His Arg Gln Met Ala Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
            195                 200                 205

Thr Arg Gln Met Val His Ala Met Arg Thr Ile Gly Thr His Pro Ser
        210                 215                 220

Ser Ser Ala Gly Leu Lys Asp Asp Leu Leu Glu Asn Leu Gln Ala Tyr
225                 230                 235                 240

Gln Lys Arg Met Gly Val Gln Ile Gln Arg Phe Lys
                245                 250
```

COMPOSITIONS AND METHODS FOR GENERATING AN IMMUNE RESPONSE TO HEPATITIS B VIRUS

CROSS REFERENCE TO RELATED APPLICATIONS

This application is a continuation of U.S. patent application Ser. No. 16/305,305, filed on Nov. 28, 2018, which is a national stage application under 35 U.S.C. § 371 of International Application No. PCT/US2017/034983, filed May 30, 2017, which claims the benefit of U.S. Provisional Application No. 62/343,074, filed May 30, 2016, each of which is incorporated by reference herein in its entirety.

FIELD OF THE INVENTION

The present invention is directed to compositions, including vaccine compositions, for generating an immune response to a hepatitis B virus in a subject to which the composition is administered, as well as methods of manufacture and use of such compositions. More specifically, the compositions and methods described herein relate to a modified vaccinia Ankara (MVA) vector encoding one or more viral antigens, suitable for use in generating a protective immune response to a hepatitis B virus in a subject to which the vector is administered. The compositions and methods of the present invention are useful both prophylactically and therapeutically.

INCORPORATION BY REFERENCE

The contents of the text file named "19101-017US2_2021-07-06_Seq_Listing_ST25.txt" which was created on Jul. 6, 2021 and is 11.4 KB in size, are hereby incorporated by reference in their entirety.

BACKGROUND OF THE INVENTION

Despite great progress in antiviral treatments, hepatitis B virus (HBV) infection is still a major global public health problem. Approximately 2 billion people have been infected worldwide during their lifetime, and more than 350 million are chronic carriers of the virus (Liaw Y F, et al. Lancet 2009, 373:582-592). HBV is not cytopathic per se, but the host antiviral immune response to envelope, capsid and Pol proteins results in hepatocyte damage. Specifically, $CD4^+$ and $CD8^+$ T-cell responses have been shown to play a central role in the outcome of infection. (Bauer T et al., Dig. Dis. 2011; 29:423-433) Various studies have shown that $CD4^+$ helper T-cell- and $CD8^+$ cytotoxic T-cell-mediated immune responses determine the outcome of HBV infection. Thus, spontaneous viral clearance of HBV infection is characterized by vigorous and sustained multi-epitope-specific $CD4^+$ and $CD8^+$ T-cell responses during the acute phase of infection. In contrast, chronic infection with HBV is correlated with late, transient, weak or narrowly focused $CD4^+$ and $CD8^+$ T-cell responses. (Ferrari C. et al., J Immunol. 1990; 145:3442-3449; Rehermann B. et al., J Exp Med. 1995; 181:1047-1058) However, it is important to note that the effects of $CD4^+$ and $CD8^+$ T-cell responses are not only important for viral control but also implicated in liver injury and the establishment of liver diseases in HBV infections. (Maini M K, et al., J Exp Med. 2000; 191:1269-1280) HBV infection may cause acute and chronic hepatitis, which leads to liver cirrhosis (LC) and hepatocellular carcinoma (HCC) (Chu C M. J Gastroenterol Hepatol 2000 15 Suppl:E25-30).

Not all available HBV vaccines are broadly effective. Current HBV vaccines on the market, which protect most people prophylactically against HBV infection contain only the S. antigen. Almost 5 to 10% people vaccinated prophylactically with the available vaccines fail to mount an adequate antibody response to offer protection (Kubba A K, et al. Commun Dis Public Health 2003 6: 106-112). Furthermore, no HBV vaccine currently available is effective therapeutically. Once an HBV infection becomes established as a chronic infection, mounting an effective immune response against the virus becomes still more difficult because the immune system grows tolerant to the persisting virus.

What is needed is a vaccine or immune response stimulating composition to break tolerance to the hepatitis B surface antigen (HBsAg/Australia antigen) and other HBV antigens, to induce anti-HBsAg neutralizing antibodies, and to induce productive $CD4^+$ and $CD8^+$ T cell responses.

SUMMARY OF THE INVENTION

The compositions and methods of the invention described herein are useful for generating an immune response to at least one hepatitis B virus in a subject in need thereof. Advantageously, the compositions and methods may be used prophylactically to immunize a subject against a hepatitis B virus infection, or used therapeutically to prevent, treat or ameliorate the onset and severity of disease.

In a first aspect, the present invention is a recombinant modified vaccinia Ankara (MVA) vector comprising one or more nucleic acid sequence encoding a hepatitis B virus polypeptide or fusion protein, wherein the at least one nucleic acid sequence is inserted into the MVA vector under the control of at least one promoter compatible with a poxvirus expression system.

In one embodiment, the recombinant MVA vector comprises two or more nucleic acid sequences encoding hepatitis B virus proteins, wherein the at least two nucleic sequences are inserted into the MVA vector under the control of at least two promoters capable compatible with poxvirus expression systems.

In one embodiment, the recombinant MVA vector comprises a first nucleic acid sequence encoding one or more hepatitis structural proteins and a second nucleic sequence encoding one or more hepatitis B nonstructural proteins, wherein both the first and second nucleic acid sequences are inserted into the MVA vector under the control of promoters compatible with poxvirus expression systems.

In one embodiment, the hepatitis B virus structural protein comprises PreS2-S protein or fragments thereof.

In some embodiments, the hepatitis B virus structural protein comprises a fragment of the PreS2-S protein lacking all or part of the S domain.

In one embodiment, the hepatitis B virus structural protein is a fusion protein.

In one embodiment, the hepatitis B virus structural protein is a preS.HA fusion protein. In one embodiment, the hepatitis B virus non-structural protein are selected from PreC-C, and truncated X protein, and fragments thereof.

In one embodiment, the hepatitis B virus non-structural protein are selected from PreC-C, and X protein, and fragments thereof.

In one embodiment, the hepatitis B virus non-structural protein is a fusion protein.

In one embodiment, the hepatitis B virus non-structural protein is M1.P41A.

In one embodiment, the first and second nucleic acid sequences are inserted into one or more deletion sites of the recombinant MVA vector.

In one embodiment, the first and second nucleic acid sequences are inserted into the recombinant MVA vector in a natural deletion site, a modified natural deletion site, or between essential or non-essential MVA genes.

In another embodiment, the first and second nucleic acid sequences are inserted into the same natural deletion site, a modified natural deletion site, or between the same essential or non-essential MVA genes.

In another embodiment, the first nucleic acid sequence is inserted into a deletion site selected from I, II, III, IV, V or VI and the nonstructural protein sequence is inserted into a deletion site selected from I, II, III, IV, V or VI.

In another embodiment, the first nucleic sequence is inserted in a first deletion site and the second nucleic acid sequence is inserted into a second deletion site.

In a particular embodiment, the first nucleic acid sequence is inserted between two essential and highly conserved MVA genes and the second nucleic acid sequence is inserted into a restructured and modified deletion site III.

In a particular embodiment, the first nucleic acid sequence is inserted between two essential and highly conserved MVA genes to limit the formation of viable deletion mutants.

In a particular embodiment, the first nucleic acid sequence is inserted between MVA genes, I8R and G1L.

In a particular embodiment, the first nucleic acid sequence is inserted between MVA genes, I8R and G1L and the second nucleic acid sequence is inserted into modified deletion site III.

In one embodiment, the promoter is selected from the group consisting of Pm2H5, PsynII, mH5 promoters, or combinations thereof.

In one embodiment, the recombinant MVA vector expresses one or more structural proteins and non-structural proteins that assemble into VLPs.

In one embodiment, the structural protein sequence and the non-structural protein sequence are from a hepatitis B genotype A, B, C, D, E, F, G, or H.

In one embodiment, the structural protein sequence and the non-structural protein sequence are from a hepatitis B genotype D.

In a second aspect, the present invention is a pharmaceutical composition comprising the recombinant MVA vector of the present invention and a pharmaceutically acceptable carrier.

In one embodiment, the recombinant MVA vector is formulated for intraperitoneal, intramuscular, intradermal, epidermal, mucosal or intravenous administration.

In one embodiment, the recombinant MVA vector is formulated for intramuscular administration.

In a third aspect, the present invention is a pharmaceutical composition comprising a first recombinant MVA vector and a second recombinant MVA vector, each comprising a first nucleic acid sequence encoding a hepatitis B virus structural protein and a second nucleic acid sequence encoding a hepatitis B virus non-structural protein, wherein (i) the first nucleic acid sequence of the first recombinant MVA vector is different than the first nucleic acid sequence of the second recombinant MVA vector and/or (ii) the second nucleic acid sequence of the first recombinant MVA vector is different than the second nucleic acid sequence of the second recombinant MVA vector.

In a particular embodiment, the first nucleic sequence of the first and second recombinant MVA vector encodes PreS2_S or PreS.HA, and the first nucleic acid sequence of the first recombinant MVA vector is from the same or a different genotype than the first nucleic acid sequence of the second recombinant MVA vector.

In one embodiment, the first and second sequences of the first recombinant MVA vector are from genotype B and the first and second sequences of the second recombinant MVA vector are from genotype C.

In one embodiment, the first and second sequences of the first recombinant MVA vector are from genotype A and the first and second sequences of the second recombinant MVA vector are from genotype D.

In one embodiment, the first and second sequences of the first recombinant MVA vector are from genotype C and the first and second sequences of the second recombinant MVA vector are from genotype D.

In one embodiment, the pharmaceutical composition comprises four recombinant MVA vectors where the first and second sequences of each of the four vectors are from genotypes A, B, C, and D respectively.

In another particular embodiment, the second nucleic acid sequence of the first recombinant MVA vector is from a different genotype than the second nucleic acid sequence of the second recombinant MVA vector.

In various embodiments, the first nucleic acids sequences encoding structural proteins are selected from genotypes A, B, C, or D and the second nucleic acid sequences encoding nonstructural proteins are selected from genotypes C and D.

In a particular embodiment, the first nucleic acid sequence of each recombinant vector are from the same genotype.

In a fifth aspect, the present invention is a method of inducing an immune response in a subject in need thereof, said method comprising administering the composition of the present invention to the subject in an amount sufficient to induce an immune response.

In one embodiment, the composition is administered prophylactically to immunize a subject against hepatitis B virus infection.

In one embodiment, the composition is administered therapeutically to prevent, treat or ameliorate the onset and severity of disease.

In one embodiment, the immune response is a humeral immune response, a cellular immune response or a combination thereof.

In a particular embodiment, the immune response comprises production of binding antibodies against the hepatitis B virus.

In a particular embodiment, the immune response comprises production of neutralizing antibodies against the hepatitis B virus.

In a particular embodiment, the immune response comprises production of non-neutralizing antibodies against the hepatitis B virus.

In a particular embodiment, the immune response comprises production of a cell-mediated immune response against the hepatitis B virus.

In a particular embodiment, the immune response comprises production of a $CD8^+$ T cell response against the hepatitis B virus.

In a particular embodiment, the immune response comprises production of neutralizing and non-neutralizing antibodies against the hepatitis B virus.

In a particular embodiment, the immune response comprises production of neutralizing antibodies and cell-mediated immunity against the hepatitis B virus.

In a particular embodiment, the immune response comprises production of non-neutralizing antibodies and cell-mediated immunity against the hepatitis B virus.

In a particular embodiment, the immune response comprises production of neutralizing antibodies, non-neutralizing antibodies, and cell-mediated immunity against the hepatitis B virus.

In a particular embodiment, the immune response comprises production of neutralizing antibodies and CD8+ T cell immunity against the hepatitis B virus.

In a particular embodiment, the immune response comprises production of non-neutralizing antibodies and CD8+ T cell immunity against the hepatitis B virus.

In a particular embodiment, the immune response comprises production of neutralizing antibodies, non-neutralizing antibodies, and CD8+ T cell immunity against the hepatitis B virus.

In one embodiment, the immune response is considered a surrogate marker for protection against a hepatitis B virus.

In one embodiment, the method induces an immune response against a hepatitis B virus.

In a sixth aspect, the present invention is a method of preventing a hepatitis B virus infection in a subject in need thereof, said method comprising administering the recombinant MVA vector of the present invention to the subject in a prophylactically effective amount.

In an seventh aspect, the present invention is a method of treating hepatitis B virus infection in a subject in need thereof, said method comprising administering the recombinant MVA vector in a therapeutically effective amount to the subject.

In another embodiment, the method results in reduction or elimination of the subject's ability to transmit the infection to a subject.

In one embodiment, the method prevents or ameliorates a hepatitis B virus infection.

In an eighth aspect, the present invention is a method manufacturing a recombinant MVA vector comprising inserting at least one nucleic acid sequence encoding PreS2_S or PreS.HA and at least one nucleic acid sequence encoding a non-structural protein sequence into the recombinant MVA vector, wherein each nucleic acid sequence is operably linked to a promoter compatible with a poxvirus expression system.

In one embodiment, the non-structural sequence is PreCore/Core, truncated X gene or M1.P41A.

In one embodiment, the recombinant MVA viral vector expresses hepatitis B virus PreS2_S and PreCore/Core and Truncated X proteins that assemble into VLPs.

In one embodiment, the recombinant MVA viral vector expresses hepatitis B virus PreS2_S and M1.P41A proteins that assemble into VLPs.

The ampicillin resistance marker, allowing the vector to replicate in bacteria is illustrated with a block labeled "amp-R." The two flanking sequences, allowing the vector to recombine with the MVA genome, are illustrated with a block labeled "Flank 1" and a block labeled "Flank 2" respectively. The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of PreS2_S into the MVA genome. The modified H5 (mH5) promoter, which enables transcription of the inserted heterologous gene, is illustrated with a triangle between the DR and PreS2_S elements. The hepatitis B virus PreS2_S gene is illustrated with an arrow labeled "PreS2_S".

Figure 1:
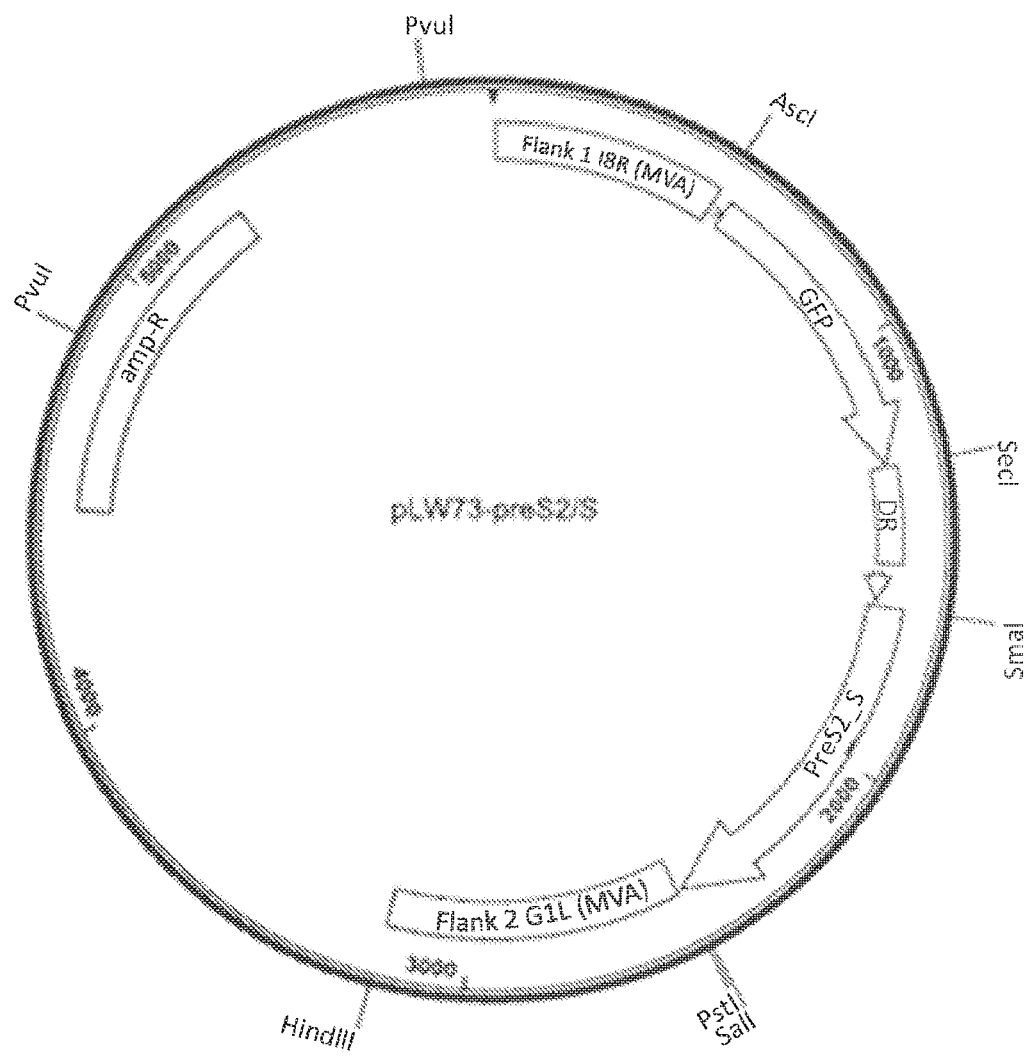
FIG. 1 is a schematic for the shuttle vector for hepatitis B virus PreS2_S.
Figure 2:
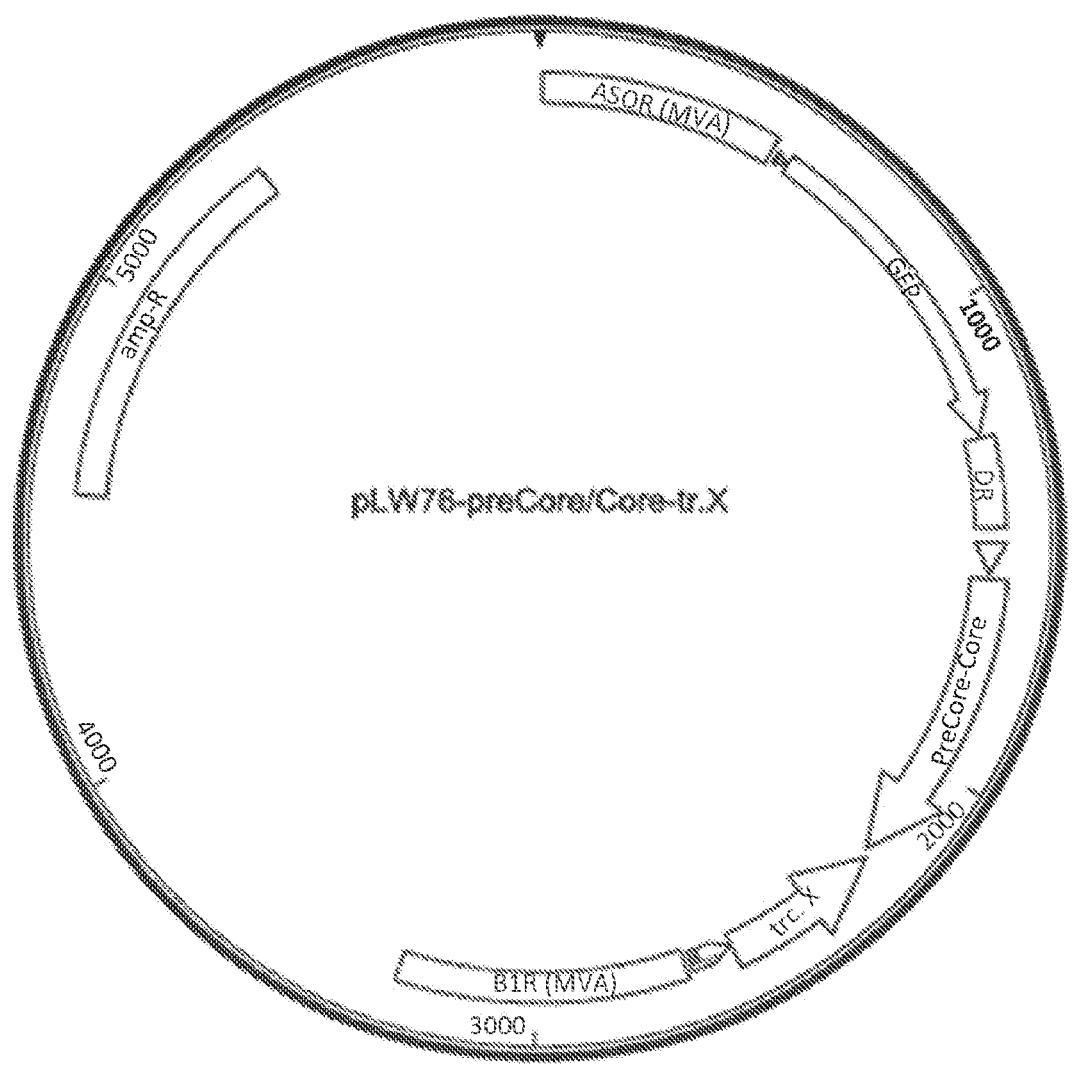

FIG. 2 is a schematic for the shuttle vector for hepatitis virus PreCore/Core_tr.X.

The ampicillin resistance marker, allowing the vector to replicate in bacteria, is illustrated with a block labeled "amp-R." The two flanking sequences, allowing the vector to recombine with the MVA genome, are illustrated with blocks labeled "A50R" and "B1R". The green fluorescent protein (GFP) selection marker, allowing the selection of recombinant MVAs, is illustrated with an arrow labeled "GFP." The block labeled "DR" illustrates the location of a sequence homologous to part of A50R of the MVA sequence. DR enables removal of the GFP sequence from the MVA vector after insertion of sequences into the MVA genome. The modified vaccinia virus P7.5 promoter, which enables transcription of the inserted heterologous gene, is illustrated with a triangle between the DR and PreCore/Core elements. The hepatitis B PreCore/Core gene is illustrated with an arrow labeled "PreCore-Core." The hepatitis B truncated X gene is illustrated with an arrow labeled "trc. X."

Figure 3:
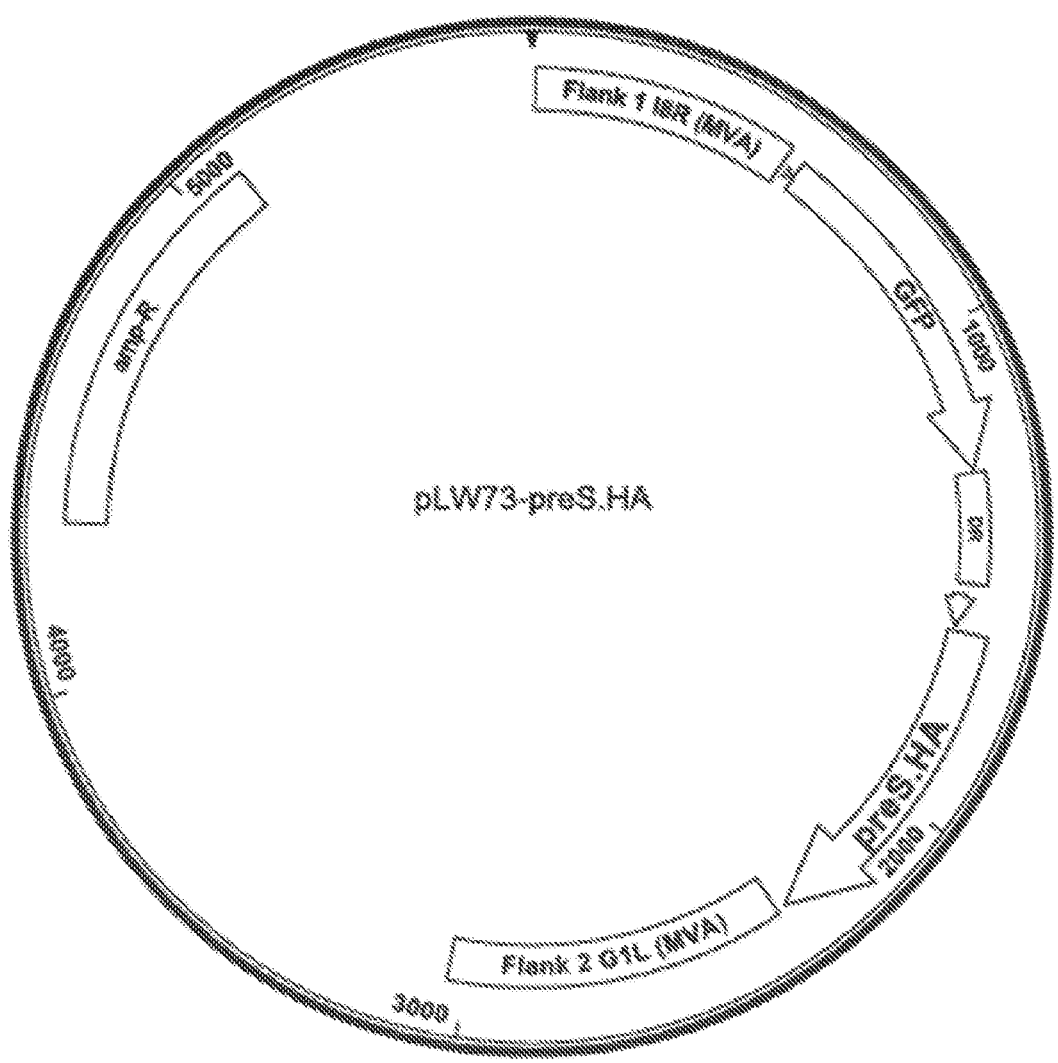

FIG. 3 is a schematic for the shuttle vector for hepatitis B fusion protein preS.HA.

The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of PreS.HA into the MVA genome. The modified H5 (mH5) promoter, which enables transcription of the inserted heterologous gene, is illustrated with a triangle between the DR and PreS.HA elements. The hepatitis B fusion protein PreS.HA gene is illustrated with an arrow labeled "PreS.HA."

Figure 4:
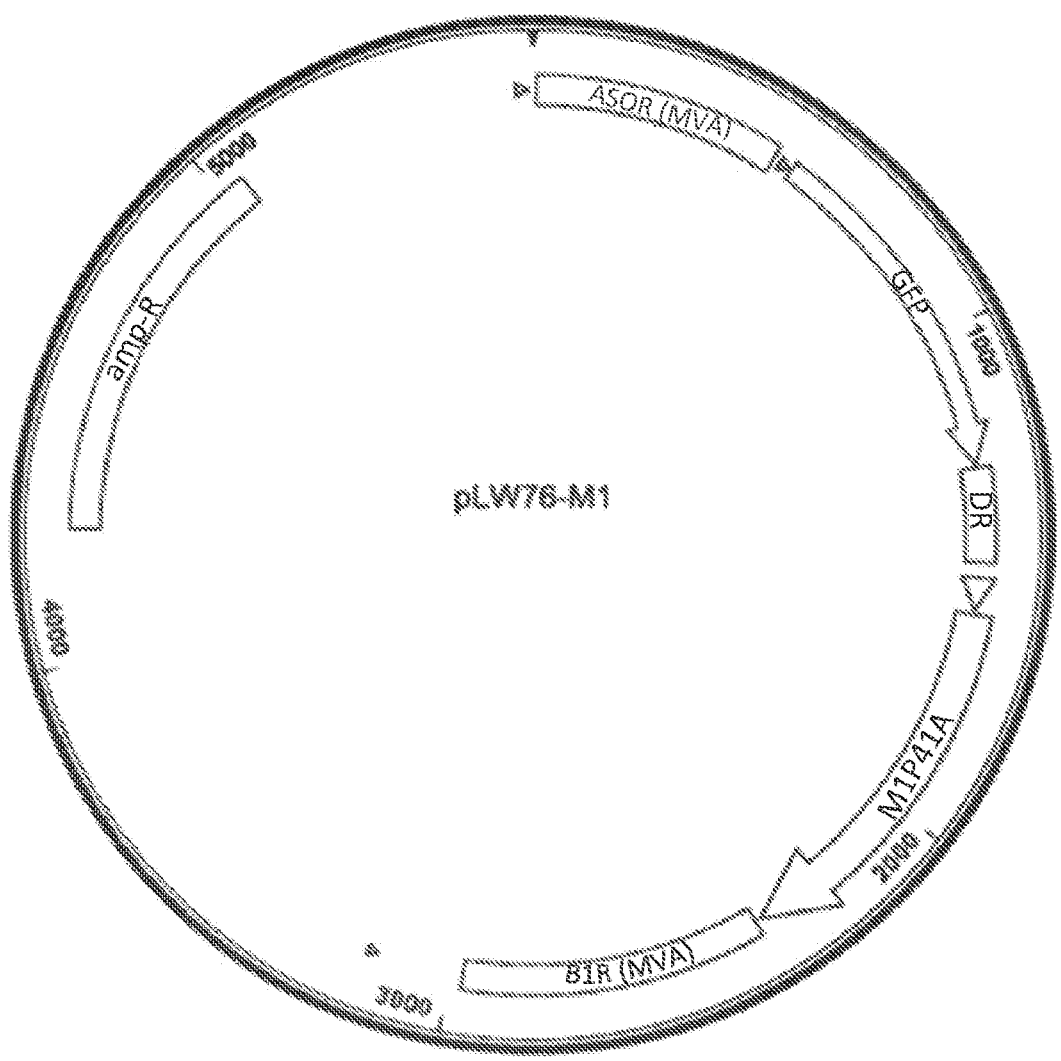

FIG. 4 is a schematic for the shuttle vector for hepatitis B fusion protein M1.P41A.

The ampicillin resistance marker, allowing the vector to replicate in bacteria, is illustrated with a block labeled "amp-R." The two flanking sequences, allowing the vector to recombine with the MVA genome, are illustrated with blocks labeled "A50R" and "B1R". The green fluorescent protein (GFP) selection marker, allowing the selection of recombinant MVAs, is illustrated with an arrow labeled "GFP." The block labeled "DR" illustrates the location of a sequence homologous to part of A50R of the MVA sequence. DR enables removal of the GFP sequence from the MVA vector after insertion of M1.P4A into the MVA genome. The modified H5 (mH5) promoter, which enables transcription of the inserted heterologous gene, is illustrated with a triangle between the DR and M1.P4A elements. The hepatitis B fusion protein M1.P4A gene is illustrated with an arrow labeled "M1.P4A."

DETAILED DESCRIPTION OF THE INVENTION

Compositions and methods are provided to produce an immune response to a hepatitis B virus, in a subject in need thereof. The compositions and methods of the present invention can be used to prevent infection in an unexposed person or to treat disease in a subject exposed to a hepatitis B virus who is not yet symptomatic or has minimal symptoms, or to treat disease in a subject with active chronic hepatitis B virus infection. In one embodiment, treatment limits an infection and/or the severity of disease.

Ideal immunogenic compositions or vaccines are safe, effective, and provide sufficient scope of protection and longevity. However, compositions having fewer than all of these characteristics may still be useful in preventing viral infection or limiting symptoms or disease progression in an exposed subject treated prior to the development of symptoms or limiting symptoms or disease progression in an exposed subject treated after to the development of symptoms. In one embodiment the present invention provides a vaccine that permits at least partial, if not complete, protection after a single immunization.

In exemplary embodiments, the immune responses are long-lasting and durable so that repeated boosters are not required, but in one embodiment, one or more administrations of the compositions provided herein are provided to boost the initial primed immune response.

I. Definitions

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a peptide" includes a plurality of peptides. Thus, for example, a reference to "a method" includes one or more methods, and/or steps of the type described herein and/or which will become apparent to those persons skilled in the art upon reading this disclosure.

The term "antigen" refers to a substance or molecule, such as a protein, or fragment thereof, that is capable of being a target of an immune response.

The term "binding antibody" or "bAb" refers to an antibody which either is purified from, or is present in, a body fluid (e.g., serum or a mucosal secretion) and which recognizes a specific antigen. As used herein, the antibody can be a single antibody or a plurality of antibodies. Binding antibodies comprise neutralizing and non-neutralizing antibodies.

The term "cell-mediated immune response" refers to the immunological defense provided by lymphocytes, such as the defense provided by sensitized T cell lymphocytes when they directly lyse cells expressing foreign antigens and secrete cytokines (e.g., IFN-gamma.), which can modulate macrophage and natural killer (NK) cell effector functions and augment T cell expansion and differentiation. The cellular immune response is one of two branches of the adaptive immune response.

The term "conservative amino acid substitution" refers to substitution of a native amino acid residue with a non-native residue such that there is little or no effect on the size, polarity, charge, hydrophobicity, or hydrophilicity of the amino acid residue at that position, and without resulting in substantially altered immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

The terms "gene", "polynucleotide", "nucleotide" and "nucleic acid" are used interchangeably herein.

The term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein.

In one embodiment, a fragment of a full-length protein retains activity of the full-length protein. In another embodiment, the fragment of the full-length protein does not retain the activity of the full-length protein.

The term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In a preferred embodiment, a fragment of a nucleic acid encodes a peptide or polypeptide that retains activity of the full-length protein. In another embodiment, the fragment encodes a peptide or polypeptide that of the full-length protein does not retain the activity of the full-length protein. As used herein, the term "hepatitis B genotype" refers to difference classifications of hepatitis B virus differentiated into many genotypes, according to genome sequence. There are eight well-known genotypes (A, B, C, D, E, F, G, H, I and J) of the HBV genome that have been identified. Genotypes C and D are recognized as being causative of more severe disease.

As used herein, the phrase "hepatitis B polypeptide" refers to any hepatitis B polypeptide or fusion protein described herein for use in generating an immune response to hepatitis B including structural polypeptides PreS2_S and PreS.HA and nonstructural polypeptides PreCore/Core, or truncated X protein or M1.P41A.

As used herein, the phrase "heterologous sequence" refers to any nucleic acid, protein, polypeptide or peptide sequence which is not normally associated in nature with another nucleic acid or protein, polypeptide or peptide sequence of interest.

As used herein, the phrase "heterologous gene insert" refers to any nucleic acid sequence that has been, or is to be inserted into the recombinant vectors described herein. The heterologous gene insert may refer to only the gene product encoding sequence or may refer to a sequence comprising a promoter, a gene product encoding sequence (such as GP, VP or Z), and any regulatory sequences associated or operably linked therewith.

The term "homopolymer stretch" refers to a sequence comprising at least four of the same nucleotides uninterrupted by any other nucleotide, e.g., GGGG or TTTTTTT.

The term "humeral immune response" refers to the stimulation of antibody (Ab) production. Humeral immune response also refers to the accessory proteins and events that accompany Ab production, including T helper cell activation and cytokine production, affinity maturation, and memory cell generation. The humeral immune response is one of two branches of the adaptive immune response.

The term "humeral immunity" refers to the immunological defense provided by antibody, such as neutralizing Ab that can directly block infection; or, binding Ab that identifies a virus or infected cell for killing by such innate immune responses as complement (C')-mediated lysis, phagocytosis, and natural killer cells.

The term "immune" or "immunity" refers to protection from disease (e.g., preventing or attenuating (e.g., suppression) of a sign, symptom or condition of the disease) upon exposure to a pathogen (e.g., a virus) capable of causing the disease.

The term "immune response" refers to any response to an antigen or antigenic determinant by the immune system of a subject (e.g., a human). Exemplary immune responses include humeral immune responses (e.g., production of antigen-specific antibodies) and cell-mediated immune responses (e.g., production of antigen-specific T cells).

The term "immunogen" refers to a substance or molecule, such as a virus, a protein, or fragment thereof, that can induce an immune response.

The term "immunogenic" refers to the capability of a substance or molecule, such as a virus, a protein, or fragment thereof, to induce an immune response.

The term "improved therapeutic outcome" relative to a subject diagnosed as infected with a particular virus (e.g., a hepatitis B virus) refers to a slowing or diminution in the growth of virus, or viral load, or detectable symptoms associated with infection by that particular virus; or a reduction in the ability of the infected subject to transmit the infection to another, uninfected subject.

The term "inducing an immune response" means eliciting a humeral response (e.g., the production of antibodies) or a cellular response (e.g., the activation of T cells) directed against a virus (e.g., hepatitis B virus) or other immunogen in a subject to which the composition (e.g., a vaccine) has been administered.

The term "insertion" in the context of a polypeptide or protein refers to the addition of one or more non-native amino acid residues in the polypeptide or protein sequence. Typically, no more than about from 1 to 6 residues (e.g., 1 to 4 residues) are inserted at any one site within the polypeptide or protein molecule. The term "insertion" in the context of a polynucleotide or nucleic acid refers to the addition of one or more non-native nucleic acid residues in the polynucleotide or nucleic acid sequence. Typically, no more than about from 1 to 10,000 residues are inserted at any one site within the polynucleotide or nucleic acid molecule.

The term "modified vaccinia Ankara," "modified vaccinia ankara," "Modified Vaccinia Ankara," or "MVA" refers to a highly-attenuated strain of vaccinia virus developed by Dr. Anton Mayr by serial passage on chick embryo fibroblast cells; or variants or derivatives thereof. MVA is reviewed in (Mayr, A. et al. 1975 Infection 3:6-14; Swiss Patent No. 568,392).

The term "neutralizing antibody" or "NAb" refers to an antibody which is either purified from, or is present in, a body fluid (e.g., serum or a mucosal secretion) and which recognizes a specific antigen and inhibits the effect(s) of the antigen in the subject (e.g., a human). As used herein, the antibody can be a single antibody or a plurality of antibodies.

The term "non-neutralizing antibody" or "nnAb" refers to a binding antibody that is not a neutralizing antibody.

The term "operably linked", when used with reference to a promoter, refers to a configuration in which the promoter is placed at an appropriate position relative to the coding sequence of a polynucleotide such that the promoter directs expression of the coding sequence.

The term "prevent", "preventing" and "prevention" refers to the inhibition of the development or onset of a condition (e.g., a hepatitis B infection or a condition associated therewith), or the prevention of the recurrence, onset, or development of one or more symptoms of a condition in a subject resulting from the administration of a therapy or the administration of a combination of therapies.

The term "prophylactically effective amount" refers to the amount of a composition (e.g., the recombinant MVA vector or pharmaceutical composition) which is sufficient to result in the prevention of the development, recurrence, or onset of a condition or a symptom thereof (e.g., a hepatitis B infection or a condition or symptom associated therewith) or to enhance or improve the prophylactic effect(s) of another therapy.

The term "recombinant" means a polynucleotide of semi-synthetic, or synthetic origin that either does not occur in nature or is linked to another polynucleotide in an arrangement not found in nature.

The term "recombinant," with respect to a viral vector, means a vector (e.g., a viral genome) that has been manipulated in vitro (e.g., using recombinant nucleic acid techniques) to express heterologous viral nucleic acid sequences.

The term "regulatory sequence" or "regulatory sequences" refers collectively to promoter sequences, polyadenylation signals, transcription termination sequences, upstream regulatory domains, origins of replication, internal ribosome entry sites ("IRES"), enhancers, and the like, which collectively provide for the transcription and translation of a coding sequence. Not all of these control sequences need always be present so long as the selected gene is capable of being transcribed and translated.

The term "shuttle vector" refers to a genetic vector (e.g., a DNA plasmid) that is useful for transferring genetic material from one host system into another. A shuttle vector can replicate alone (without the presence of any other vector) in at least one host (e.g., E. coli). In the context of MVA vector construction, shuttle vectors are usually DNA plasmids that can be manipulated in E. coli and then introduced into cultured cells infected with MVA vectors, resulting in the generation of new recombinant MVA vectors.

The term "silent mutation" means a change in a nucleotide sequence that does not cause a change in the primary structure of the protein encoded by the nucleotide sequence, e.g., a change from AAA (encoding lysine) to AAG (also encoding lysine).

The term "subject" means any mammal, including but not limited to, humans, domestic and farm animals, and zoo, sports, or pet animals, such as dogs, horses, cats, cows, rats, mice, guinea pigs and the like.

The term "surrogate endpoint" means a clinical measurement other than a measurement of clinical benefit that is used as a substitute for a measurement of clinical benefit.

The term "surrogate marker" means a laboratory measurement or physical sign that is used in a clinical or animal trial as a substitute for a clinically meaningful endpoint that is a direct measure of how a subject feels, functions, or survives and is expected to predict the effect of the therapy (Katz, R., NeuroRx 1:189-195 (2004); New drug, antibiotic, and biological drug product regulations; accelerated approval-FDA. Final rule. Fed Regist 57: 58942-58960, 1992.).

The term "surrogate marker for protection" means a surrogate marker that is used in a clinical or animal trial as a substitute for the clinically meaningful endpoint of prevention of hepatitis B virus infection.

The term "synonymous codon" refers to the use of a codon with a different nucleic acid sequence to encode the same amino acid, e.g., AAA and AAG (both of which encode lysine). Codon optimization changes the codons for a protein to the synonymous codons that are most frequently used by a vector or a host cell.

The term "therapeutically effective amount" means the amount of the composition (e.g., the recombinant MVA vector or pharmaceutical composition) that, when administered to a mammal for treating an infection, is sufficient to effect treatment for the infection.

The term "treating" or "treat" refer to the eradication or control of a hepatitis B virus, a reduction in the titer of the hepatitis B virus, a reduction in the numbers of the hepatitis B virus, the reduction or amelioration of the progression, severity, and/or duration of a condition or one or more symptoms caused by the hepatitis B virus resulting from the administration of one or more therapies, or the reduction or elimination of the subject's ability to transmit the infection to another uninfected subject.

The term "vaccine" means material used to provoke an immune response and confer immunity after administration of the material to a subject. Such immunity may include a cellular or humeral immune response that occurs when the subject is exposed to the immunogen after vaccine administration.

The term "vaccine insert" refers to a nucleic acid sequence encoding a heterologous sequence that is operably linked to a promoter for expression when inserted into a recombinant vector. The heterologous sequence may encode a hepatitis B protein described here.

The term "viral infection" means an infection by a viral pathogen (e.g., a hepatitis B virus) wherein there is clinical evidence of the infection based on symptoms or based on the demonstration of the presence of the viral pathogen in a biological sample from the subject.

The term "virus-like particles" or "VLP" refers to a structure which resembles the native virus antigenically and morphologically.

II. Hepatitis B Virus Genotypes and Sequences

The compositions of the present invention are useful for inducing an immune response to a hepatitis B virus.

There are 10 identified genotypes of hepatitis B virus (genotypes A, B, C, D, E, F, G, H, I, and J).

In one embodiment, sequences corresponding to genotypes C or D are employed in the MVA vectors described herein. Genotypes C and D are recognized as causing more severe disease.

In one embodiment, sequences corresponding to genotype D are employed in the MVA vectors described herein.

In another embodiment, sequences corresponding to genotypes B and C are employed in the MVA vectors described herein.

In another embodiment, sequences corresponding to genotypes A and D are employed in the MVA vectors described herein.

In another embodiment, sequences corresponding to genotypes A, B, C, and D are employed in the MVA vectors described herein.

There are four known genes encoded by the genome called C, P, S, and X. The core protein is coded for by gene C (HBcAg), and its start codon is preceded by an upstream in-frame AUG start codon from which the pre-core protein is produced. HBcAg is produced by proteolytic processing of the pre-core protein. The DNA polymerase is encoded by gene P. Gene S is the gene that codes the surface antigen (HBsAg). The HBsAg gene is one long open reading frame but contains three in frame "start" (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. The function of the protein coded for by gene X is not fully understood, but some evidence suggests that it may function as a transcriptional transactivator.

A. Antigen Sequences Used in MVA Vectors

In one embodiment, the MVA vector expresses a polypeptide comprising a hepatitis B preS2_S epitope, or an antigenic fragment thereof, can provide B and T cell epitopes that promote the humeral and cellular responses and enhance the seroprotection rate by overcoming non-responsiveness to the S antigen-only vaccines. Therefore, compositions and methods are disclosed using a preS antigen to develop vaccines and immune therapies for treating or preventing hepatitis B infection.

In some embodiments, a preS2_S sequence is incorporated into an MVA vector, which when expressed produce virus-like particle (VLP) that can be used, for example, as a vaccine.

In some embodiments, a preCore/Core sequence is incorporated into an MVA vector, which when expressed produce VLP that can be used, for example, as a vaccine that elicits Ab responses or T cell responses or Ab and T cell responses.

In some embodiments, a truncated X sequence is incorporated into an MVA vector, which when expressed produces truncated X protein that can be used, for example, as a vaccine that elicits Ab responses or T cell responses or Ab and T cell responses.

In some embodiments, a PreS.HA and a M1.P41A sequence is incorporated into an MVA vector, which when expressed produce VLP that can be used, for example, as a vaccine that elicits Ab responses or T cell responses or Ab and T cell responses.

| Antigen epitopes | Sequence |
| --- | --- |
| PreS2-S (PreS 55AA + S 212AA) | SEQ ID N0: 1 |
| PreC-C (PreC 29AA + C 183AA) | SEQ ID N0: 2 |
| Truncated X protein (including MHCI and MHCII epitopes) | SEQ ID N0: 3 |

| Antigen epitopes | Sequence |
|---|---|
| PreS.HA | SEQ ID N0: 4 |
| M1.P41A | SEQ ID N0: 5 |

B. Hepatitis B preS.HA Fusion Protein

In some embodiments, the hepatitis B virus structural protein comprises a fragment of the PreS2-S protein lacking all or part of the S domain (i.e., the preS antigen). The S domain can therefore be replaced with an alternative transmembrane domain in some embodiments. For example, a fusion protein is disclosed that comprises a hepatitis B preS antigen fused at the N-terminus to a transmembrane domain and optional cytoplasmic tail of a viral envelope protein. Viral envelope proteins that contain transmembrane domains suitable for VLP formation include influenza virus hemagglutinin (HA) protein, a type I transmembrane protein. The hepatitis B preS antigen may also be fused with other type I transmembrane glycoproteins, such as glycoproteins from arenaviruses, bunyaviruses, coronaviruses, filoviruses, paramyxoviruses, retroviruses, and togaviruses.

In one embodiment, the MVA vector expresses a fusion protein comprising a hepatitis B preS epitope fused to the HA protein, or an antigenic fragment thereof, can provide B and T cell epitopes that promote the humeral and cellular responses and enhance the seroprotection rate by overcoming non-responsiveness to the S antigen-only vaccines. Therefore, compositions and methods are disclosed using a preS antigen to develop vaccines and immune therapies for treating or preventing hepatitis B infection.

In some embodiments, a preS fusion antigen is incorporated into a virus-like particle (VLP) that can be used, for example, as a vaccine or to active T cells. In one embodiment, the preS antigen can be incorporated into a fusion protein that will incorporate into a VLP. For example, a fusion protein is disclosed that comprises a hepatitis B preS antigen fused at the N-terminus to a transmembrane domain and optional cytoplasmic tail of a viral envelope protein.

In one embodiment, the expressed hepatitis B preS antigen has the amino acid sequence: MGTNLSVPNPLGFFPDHQLDPAFGANSNNPDWDFNPIKDHWPAANQVGVGAFGPG LTPPHGGILGWSPQAQGILTTVSTIPPPASTNRQS-GRQPTPISPPLRDSHPQAMQWNSTAF HQALQDP RVRGL YLPAG GSSSGTVNPA PNIASHISSI-SARTGDPVTN (SEQ ID NO: 6), or a conservative variant thereof having at least about 70%, 80%, or 90% sequence identity to SEQ ID NO: 6 (i.e., one, two, or three conservative amino acid substitutions).

In some embodiments, the disclosed HBVpreS.HA (SHA) fusion protein corresponding to the nucleotide sequence of SEQ ID NO:4 has the amino acid sequence: MEAK-LFVLFC AFT ALKAMGT NLSVPNPLGF FPDHQLDP AF GANSNNPDWDFNPIKDHWPA ANQVGVGAFG PGL TPPHGGI LGWSPQAQGI LTTVSTIPPPASTNRQS-GRQ PTPISPPLRD SHPQAMQWNS TAFHQALQDP RVRGL YLPAGGSSSGTVNPA PNIASHISSI SARTGDPVTN KLESVGVHQI LAIYSTVASSL VLL VSLGAI SFWMCSNGSL QCRICI (SEQ ID NO:7), or a conservative variant thereof having at least about 70%, 80%, or 90% sequence identity to SEQ ID NO:7 (i.e., one, two, or three conservative amino acid substitutions).

In some embodiments, the influenza virus M1.P41A protein has the amino acid sequence corresponding to the translated nucleotide sequence of SEQ ID NO:5: MSLL TEVETY VLSIIPSGPL KAEIAQRLEG VF AGKNTDL-EALMEWLKTRP ILSPLTKGIL GFVFTLTVPS ERGLQRRRFV QNALNGNGDPNNMDRA VKL Y KKLKREITFH GAKEVSLSYS TGALASCMGL IYNRMGTVTTEAAFGLVCAT CEQIADSQHR SHRQMATTTN PLIRHENRMV LASTTAKAM EQMAGSSEQAAEAMEVASQTRQMVHAM RTIGTH-PSSSAGLKDDLLENLQAYQK RMGVQIQRFK (SEQ ID NO:8), or a conservative variant thereof having at least about 70%, 80%, or 90% sequence identity to SEQ ID NO:8 (i.e., one, two, or three conservative amino acid substitutions).

III. Recombinant Viral Vectors

In one aspect, the present invention is a recombinant viral vector comprising one or more genes of a hepatitis B virus. In certain embodiments, the recombinant viral vector is a vaccinia viral vector, and more particularly, an MVA vector, comprising one or more genes of ahepatitis B virus.

Vaccinia viruses have also been used to engineer viral vectors for recombinant gene expression and for the potential use as recombinant live vaccines (Mackett, M. et al 1982 PNAS USA 79:7415-7419; Smith, G. L. et al. 1984 Biotech Genet Engin Rev 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385). The recombinant vaccinia viruses prepared in this way can be used, on the one hand, as live vaccines for the prophylaxis of infectious diseases, on the other hand, for the preparation of heterologous proteins in eukaryotic cells.

Several such strains of vaccinia virus have been developed to avoid undesired side effects of smallpox vaccination. Thus, a modified vaccinia Ankara (MVA) has been generated by long-term serial passages of the Ankara strain of vaccinia virus (CVA) on chicken embryo fibroblasts (for review see Mayr, A. et al. 1975 Infection 3:6-14; Swiss Patent No. 568,392). The MVA virus is publicly available from American Type Culture Collection as ATCC No.: VR-1508. MVA is distinguished by its great attenuation, as demonstrated by diminished virulence and reduced ability to replicate in primate cells, while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 J Gen Virol 72:1031-1038). The resulting MVAvirus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr A. et al. 1978 Zentralbl Bakteriol [B] 167:375-390; Stickl et al. 1974 Dtsch Med Wschr 99:2386-2392). During these studies in over 120,000 humans, including high-risk patients, no side effects were associated with the use of MVA vaccine.

MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. 1992 PNAS USA 89:10847-10851). Additionally, novel vaccinia vector vaccines were established based on MVA having foreign DNA sequences inserted at the site of deletion III within the MVA genome (Sutter, G. et al. 1994 Vaccine 12:1032-1040).

Recombinant MVA vaccinia viruses can be prepared as set out hereinafter. A DNA-construct which contains a DNA-sequence which codes for a foreign polypeptide flanked by MVA DNA sequences adjacent to a predetermined insertion site (e.g., between two conserved essential MVA genes such as I8R/G1L; in restructured and modified deletion III; or at other non-essential sites within the MVA genome) is introduced into cells infected with MVA, to allow homologous recombination. Once the DNA-construct has been introduced into the eukaryotic cell and the foreign DNA has recombined with the viral DNA, it is possible to isolate the desired recombinant vaccinia virus in a manner known per se, preferably with the aid of a marker. The DNA-construct to be inserted can be linear or circular. A plasmid or polymerase chain reaction product is preferred. Such methods of making recombinant MVA vectors are described in PCT publications WO/2006/026667 and WO/2016/115116 incorporated by reference herein. The DNA-construct contains sequences flanking the left and the right side of a naturally occurring deletion. The foreign DNA sequence is inserted between the sequences flanking the naturally occurring deletion. For the expression of a DNA sequence or gene, it is necessary for regulatory sequences, which are required for the transcription of the gene, to be present on the DNA. Such regulatory sequences (called promoters) are known to those skilled in the art, and include for example those of the vaccinia 11 kDa gene as are described in EP-A-198,328, and those of the 7.5 kDa gene (EP-A-110,385). The DNA-construct can be introduced into the MVA infected cells by transfection, for example by means of calcium phosphate precipitation (Graham et al. 1973 Virol 52:456-467; Wigler et al. 1979 Cell 16:777-785), by means of electroporation (Neumann et al. 1982 EMBO J. 1:841-845), by microinjection (Graessmann et al. 1983 Meth Enzymol 101:482-492), by means of liposomes (Straubinger et al. 1983 Meth Enzymol 101:512-527), by means of spheroplasts (Schaffher 1980 PNAS USA 77:2163-2167) or by other methods known to those skilled in the art.

The MVA vectors described and tested herein were unexpectedly found to be effective after a single prime or a homologous prime/boost regimen. Other MVA vector designs require a heterologous prime/boost regimen, while still other published studies have been unable to induce effective immune responses with MVA vectors. Conversely, the present MVA vector design and methods of manufacture are useful in producing effective MVA vaccine vectors for eliciting effective T-cell and antibody immune responses. Furthermore, the utility of an MVA vector capable of eliciting effective immune responses and antibody production after a single homologous prime boost is significant for considerations such as use, commercialization and transport of materials especially to affected third world locations.

In one embodiment, the present invention is a recombinant viral vector (e.g., an MVA vector) comprising one or more heterologous gene inserts of a hepatitis B virus. The viral vector (e.g., an MVA vector) may be constructed using conventional techniques known to one of skill in the art. The one or more heterologous gene inserts encode a polypeptide having desired immunogenicity, i.e., a polypeptide that can induce an immune reaction, cellular immunity and/or humeral immunity, in vivo by administration thereof. The gene region of the vector (e.g., an MVA vector) where the gene encoding a polypeptide having immunogenicity is introduced is flanked by regions that are indispensable. In the introduction of a gene encoding a polypeptide having immunogenicity, an appropriate promoter may be operatively linked upstream of the gene encoding a polypeptide having desired immunogenicity.

The one or more genes may be selected from hepatitis B virus. In one embodiment, the one more genes are selected from a hepatitis B virus genotype. In exemplary embodiments, the gene encodes a polypeptide or protein capable of inducing an immune response in the subject to which it is administered, and more particularly, an immune response capable of providing a protective and/or therapeutic benefit to the subject. In one embodiment, the one or more genes encode the virus premembrane protein PreS2_S, PreS.HA or one or more nonstructural proteins PreCore/Core, truncated X, or M1.P41A. The heterologous gene inserts are inserted into one or more deletion sites of the vector under the control of promoters compatible with poxvirus expression systems or into a site between two conserved essential MVA gene (e.g., 18R and G1L) of the vector under the control of promoters compatible with poxvirus expression systems.

In one embodiment, the deletion Ill site is restructured and modified to remove non-essential flanking sequences.

In exemplary embodiments, the vaccine is constructed to express a hepatitis B virus PreS2_S protein (PrS2_S), which is inserted between two conserved essential MVA genes (18R and G1L) using shuttle vector pLW73-preS2_S; and to express hepatitis B virus PreCore/Core/Truncated X, which is inserted into deletion Ill using shuttle vector pLW76-preCore/Core-tr.X. These two shuttle vectors are constructed with an ampicillin resistance marker, allowing the vector to replicate in bacteria; with two flanking sequences, allowing the vector to recombine with a specific location in the MVA genome; with a green fluorescent protein (GFP) selection marker, allowing the selection of recombinant MVAs; with a sequence homologous to part of Flank 1 of the MVA sequence, enabling removal of the GFP sequence from the MVA vector after insertion of nonstructural gene into the MVA genome; with a modified HS (mH5) promoter, which enables transcription of the inserted heterologous gene insert or with another promoter which enables transcription of the inserted heterologous gene insert; and with a hepatitis B gene.

In certain embodiments, the polypeptide, or the nucleic acid sequence encoding the polypeptide, may have a mutation or deletion (e.g., an internal deletion, truncation of the amino- or carboxy-terminus, or a point mutation).

The one or more genes introduced into the recombinant viral vector are under the control of regulatory sequences that direct its expression in a cell.

The nucleic acid material of the viral vector may be encapsulated, e.g., in a lipid membrane or by structural proteins (e.g., capsid proteins), that may include one or more viral polypeptides.

In exemplary embodiments, the present invention is a recombinant viral vector (e.g., a recombinant MVA vector) comprising one or more genes, or one or more polypeptides encoded by the gene or genes, from a hepatitis B virus. The hepatitis B virus gene may encode a polypeptide or protein capable of inducing an immune response in the subject to which it is administered, and more particularly, an immune response capable of providing a protective and/or therapeutic benefit to the subject.

In certain embodiments, the one or more genes encodes a polypeptide, or fragment thereof, that is substantially identical (e.g., at least 60%, 65%, 70%, 75%, 80%, 85%, 90%, 95%, 98%, 99%, or 100% identical) to the selected hepatitis B virus PreS2_S over at least 20, 25, 30, 35, 40, 45, 50, 55, 60, 65, or 70 contiguous residues of the selected hepatitis B virus PreS2_S that retain immunogenic activity.

In certain embodiments, the one or more genes encodes a polypeptide, or fragment thereof, that is substantially identical (e.g., at least 60%, 65%, 70%, 75%, 80%, 85%, 90%, 95%, 98%, 99%, or 100% identical) to the selected hepatitis B virus fusion protein M1.P41A over at least 20, 25, 30, 35, 40, 45, 50, 55, 60, 65, or 70 contiguous residues of the selected hepatitis B virus fusion protein M1.P41A that retains immunogenic activity.

In one embodiment, the structural protein or fusion protein sequence is inserted into deletion site I, II, III, IV, V or VI of the MVA vector, and the nonstructural protein or fusion protein sequence is inserted into deletion site I, II, III, IV, V or VI of the MVA vector.

In one embodiment, the structural protein or fusion protein sequence is inserted between I8R and Gil, of the MVA vector, or into restructured and modified deletion Ill of the MVA vector; and the nonstructural protein or fusion protein sequence is inserted between I8R and Gil, of the MVA vector, or into restructured and modified deletion site Ill of the MVA vector.

In exemplary embodiments, the present invention is a recombinant MVA vector comprising at least one heterologous gene insert (e.g., one or more gene inserts) from a hepatitis B virus which is under the control of regulatory sequences that direct its expression in a cell. The gene may be, for example, under the control of a promoter selected from the group consisting of Pm2H5, Psyn II, or mH5 promoters.

One or more genes may be optimized for use in the MVA vector. Optimization includes codon optimization, which employs silent mutations to change selected codons from the native sequences into synonymous codons that are optimally expressed by the host-vector system. Other types of optimization include the use of silent mutations to interrupt homopolymer stretches or transcription terminator motifs. Each of these optimization strategies can improve the stability of the gene, improve the stability of the transcript, or improve the level of protein expression from the gene. In exemplary embodiments, the number of homopolymer stretches in the sequence is reduced to stabilize the construct. A silent mutation may be provided for anything similar to a vaccinia termination signal.

In exemplary embodiments, optimization of genes may include interrupting homopolymer sequences ($\geq 4$ G/C and $\geq$A/T) by silent mutations, adding a second TAA stop codon, or adding a Vaccinia Transcription Terminator Sequence at the end of the gene such as TTTTTAT.

In exemplary embodiments, the hepatitis structural or nonstructural sequences are codon optimized for expression in MVA using a computer algorithm; PrM-E and NS1 sequences with runs of $\geq 5$ deoxyguanosines, $\geq 5$ deoxycytidines, $\geq 5$ deoxyadenosines, and $\geq 5$ deoxythymidines are interrupted by silent mutation to minimize loss of expression due to frame shift mutations.

The recombinant viral vectors of the present invention may be used alone or in combination. In one embodiment, two different recombinant viral vectors are used in combination, where the difference may refer to the one or more heterologous gene inserts or the other components of the recombinant viral vector or both. In exemplary embodiments, two or more recombinant viral vectors are used in combination in order to protect against infection by hepatitis B in humans.

The present invention also extends to host cells comprising the recombinant viral vector described above, as well as isolated virions prepared from host cells infected with the recombinant viral vector.

IV. Pharmaceutical Composition

The recombinant viral vectors of the present invention are readily formulated as pharmaceutical compositions for veterinary or human use, either alone or in combination. The pharmaceutical composition may comprise a pharmaceutically acceptable diluent, excipient, carrier, or adjuvant.

In one embodiment, the present invention is a vaccine effective to protect and/or treat a hepatitis B virus infection comprising a recombinant MVA vector that expresses at least one hepatitis B polypeptide or an immunogenic fragment thereof. The vaccine composition may comprise one or more additional therapeutic agents.

The pharmaceutical composition may comprise 1, 2, 3, 4 or more than 4 different recombinant MVA vectors.

In a particular embodiment, the first nucleic sequence encodes PreS2_S or PreS.HA, and the first nucleic acid sequence of the first recombinant MVA vector is from the same or a different genotype than the first nucleic acid sequence of the second recombinant MVA vector.

In one embodiment, the first and second sequences of the first recombinant MVA vector are from genotype Band the first and second sequences of the second recombinant MVA-vector are from genotype C.

In one embodiment, the first and second sequences of the first recombinant MVA vector are from genotype A and the first and second sequences of the second recombinant MVA vector are from genotype D.

In one embodiment, the first and second sequences of the first recombinant MVA vector are from genotype C and the first and second sequences of the second recombinant MVA vector are from genotype D.

In one embodiment, the pharmaceutical composition comprises four recombinant MVA vectors where the first and second sequences of each of the four vectors are from genotypes A, B, C, and D respectively.

As used herein, the phrase "pharmaceutically acceptable carrier" encompasses any suitable pharmaceutical carrier, such as those suitable for parenteral administration, such as, for example, by intramuscular, intraarticular (in the joints), intravenous, intradermal, intraperitoneal, and subcutaneous routes. Examples of such formulations include aqueous and non-aqueous, isotonic sterile injection solutions, which contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. One exemplary pharmaceutically acceptable carrier is physiological saline.

Other physiologically acceptable diluents, excipients, carriers, or adjuvants and their formulations are known to those skilled in the art.

The compositions utilized in the methods described herein can be administered by a route any suitable method, e.g., parenteral, intramuscular, intraarterial, intravascular, intravenous, intraperitoneal, subcutaneous, dermal, transdermal, ocular, inhalation, buccal, sublingual, perilingual, nasal, topical administration, and oral administration. The preferred method of administration can vary depending on various factors (e.g., the components of the composition being administered and the severity of the condition being treated). Formulations suitable for oral administration may consist of liquid solutions, such as an effective amount of the composition dissolved in a diluent (e.g., water, saline, or PEG-400), capsules, sachets or tablets, each containing a predetermined amount of the vaccine. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen).

For the purposes of this invention, pharmaceutical compositions suitable for delivering a therapeutic or biologically active agent can include, e.g., tablets, gelcaps, capsules, pills, powders, lyophilized powders, granulates, suspensions, emulsions, solutions, gels, hydrogels, oral gels, pastes, eye drops, ointments, creams, plasters, drenches, delivery devices, microneedles, suppositories, enemas, injectables, implants, sprays, or aerosols. Any of these formulations can be prepared by well-known and accepted methods of art. See, for example, Remington: The Science and Practice of Pharmacy (21.sup.st ed.), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

The immunogenicity of the composition (e.g., vaccine) may be significantly improved if the composition of the present invention is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM-Matrix, DC-Chol, ODA, cytokines, and other adjuvants and derivatives thereof.

Pharmaceutical compositions according to the present invention may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$); (ii) a narrow absorption window in the gastro-intestinal tract; or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, lyophilization with encapsulation into solid dissolvable carriers, lyophilization with encapsulation into that substrates incorporated into microneedles, lyophilization with encapsulation into that substrates incorporated into microneedle patches, and liposomes.

Formulations suitable for oral administration can consist of (a) liquid solutions, such as an effective amount of the vaccine dissolved in diluents, such as water, saline or PEG 400; (b) capsules, sachets or tablets, each containing a predetermined amount of the vaccine, as liquids, solids, granules or gelatin; (c) suspensions in an appropriate liquid; (d) suitable emulsions; and (e) polysaccharide polymers such as chitins. The vaccine, alone or in combination with other suitable components, may also be made into aerosol formulations to be administered via inhalation, e.g., to the bronchi al passageways. Aerosol formulations can be placed into pressurized acceptable propellants, such as dichlorodifluoromethane, propane, nitrogen, and the like.

Suitable formulations for rectal administration include, for example, suppositories, which consist of the vaccine with a suppository base. Suitable suppository bases include natural or synthetic triglycerides or paraffin hydrocarbons. In addition, it is also possible to use gelatin rectal capsules which consist of a combination of the vaccine with a base, including, for example, liquid triglycerides, polyethylene glycols, and paraffin hydrocarbons.

Pharmaceutical compositions comprising any of the nucleic acid molecules encoding hepatitis B viral proteins of the present invention are useful to immunize a subject against disease caused by hepatitis B virus infection. Thus, this invention further provides methods of immunizing a subject against disease caused by hepatitis B infection, comprising administering to the subject an immunoeffective amount of a pharmaceutical composition of the invention. This subject may be an animal, for example a mammal, such as a primate or preferably a human.

In various embodiments, the vaccines of the present invention may also be co-administered with cytokines to further enhance immunogenicity. The cytokines may be administered by methods known to those skilled in the art, e.g., as a nucleic acid molecule in plasmid form or as a protein or fusion protein.

A. Immune Checkpoint Blockade

In various embodiments, the vaccines of the present invention may also be co-administered with checkpoint inhibitor agonists to further enhance immunogenicity.

The phenomenon of immune exhaustion was first identified in chronic lymphocytic choriomeningitis virus (LMCV) in mice and was later found to occur in other human chronic viral infections such as HIV, HCV, and HBV, as well as in various cancers. A hallmark of T cell exhaustion in both such viral infections and cancer is the increased expression of various inhibitory receptors such as programmed death-1 (PD-1), cytotoxic T-lymphocyte antigen-4 (CTLA-4), cluster of differentiation 244 (CD244), cluster of differentiation 160 (CD160), and others. In cancer immunotherapy, the use of checkpoint inhibitors such as those that block the PD-1: PD-L1 pathway has resulted in significant clinical benefits with a wide range of cancer types including melanoma, non-small cell lung cancer (NSCLC), and renal cell carcinoma (RCC). The fact that T cell exhaustion is a major factor in allowing both the progression of these cancers and the persistence of chronic viral infections like HBV suggests that checkpoint inhibitors may potentially achieve clinical benefits when used as treatments for chronic HBV.

In various embodiments, the compositions of the present invention may also be co-administered or sequentially administered with checkpoint inhibitors.

Checkpoint inhibitors act by blocking a negative regulator of T-cell activation and response and these inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ ($\alpha\beta$) T cells), CD160 (also referred to as BY55), CGEN-15049, CHK1 and CHK2 kinases, A2aR and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-LI monoclonal Antibody (Anti-B7-HI; MEDI4736), MK-3475 (PD-1 blocker), Nivolumab (anti-PDI antibody), CT-011 (anti-PD1 antibody), BY55 monoclonal antibody, AMP224 (anti-PDLI antibody), BMS-936559 (anti-PDLI antibody), MPLDL3280A (anti-PDLI antibody), MSB0010718C (anti-PDLI antibody) and Yervoy/ipilimumab (anti-CTLA-4 checkpoint inhibitor). Checkpoint protein ligands include, but are not limited to PD-LI, PD-L2, B7-H3, B7-H4, CD28, CD86 and TIM-3.

In one specific embodiment, the vectors are administered in combination with, or sequentially with immune checkpoint blockade agent that block the interaction between immune checkpoint receptor programmed cell death protein 1 (PD-1) and its ligand PDL-1. See A. Mullard, "New checkpoint inhibitors ride the immunotherapy tsunami," Nature Reviews: Drug Discovery (2013), 12:489-492. PD-1 is expressed on and regulates the activity of T-cells. Specifically, when PO-1 is unbound to PDL-1, the T-cells can engage and kill target cells. However, when PD-1 is bound to PDL-1 it causes the T-cells to cease engaging and killing target cells. Furthermore, unlike other checkpoints, PD-1 acts proximately such the PDLs are overexpressed directly on cancer cells which leads to increased binding to the PD-1 expressing T-cells.

One aspect of the present disclosure provides checkpoint inhibitors which are antibodies that can act as agonists of PD-1, thereby modulating immune responses regulated by PD-1. In one embodiment, the anti-PD-1 antibodies can be antigen-binding fragments. Anti-PD-1 antibodies disclosed herein are able to bind to human PD-1 and activate PD-1, tl thereby inhibiting the function of immune cells expressing PD-1. In one embodiment, the PD-1 agonist antibody selected from BMS 936558 (nivolumab), BMS 936559, MK 3475, MPDL 3280A, AMP 224, or Medi 4736.

In one specific embodiment, the vectors are administered in combination with, or sequentially with immune checkpoint blockade agent that inhibit CTLA-4. Suitable anti-CTLA4 antagonist agents for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 81. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al, Proc. Natl. Acad. Sci. USA, 95(17): 10067-10071 (1998); Camacho et al, J. Clin. Oncology, 22(145):Abstract No. 2505 (2004) (antibody CP-675206); Mokyr et al, Cancer Res., 58:5301-5304 (1998), and U.S. Pat. Nos. 5,977,318, 6,682,736, 7,109,003, and 7,132,281.

Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the co-stimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the co-stimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the co-stimulatory pathway, RNAi inhibitors (both single and double stranded) of CD28, CD80, CD86, CTLA4, among other members of the co-stimulatory pathway, among other anti-CTLA4 antagonists.

In one specific embodiment, the vectors are administered in combination with, or sequentially with immune checkpoint blockade agent that inhibit TIM-3. Blocking the activation of TIM-3 by a ligand, results in an increase in ThI cell activation. Furthermore, TIM-3 has been identified as an important inhibitory receptor expressed by exhausted $CD8^+$ T cells. TIM-3 has also been reported as a key regulator of nucleic acid mediated antitumor immunity. In one example, TIM-3 has been shown to be upregulated on tumor-associated dendritic cells (TADCs).

This invention also provides kits comprising the vaccines of the present invention. For example, kits comprising a vaccine and instructions for use are within the scope of this invention.

V. Method of Use

The compositions of the invention can be used as vaccines for inducing an immune response to a hepatitis B virus.

In exemplary embodiments, the present invention provides a method of preventing a hepatitis B infection to a subject in need thereof (e.g., an unexposed subject), comprising administering the composition of the present invention to the subject in a prophylactically effective amount. The result of the method is that the subject is partially or completely immunized against the virus.

In exemplary embodiments, the present invention provides a method of treating a hepatitis B infection in a subject in need thereof (e.g., an exposed subject, such as a subject who has been recently exposed but is not yet symptomatic, or a subject who has been recently exposed and is only mildly symptomatic, or a subject who has been recently exposed and is strongly symptomatic, or a subject who was long ago exposed and is weakly or strongly symptomatic), comprising administering the composition of the present invention to the subject in a therapeutically effective amount. The result of treatment is a subject that has an improved therapeutic profile.

In exemplary embodiments, the present invention provides a method of treating a hepatitis B infection in a subject in need thereof (e.g., an exposed subject who is in the chronic stages of infection), comprising administering the composition of the present invention to the subject in a therapeutically effective amount. The result of treatment is a subject that has an improved therapeutic profile.

Typically, the vaccines will be in an admixture and administered simultaneously, but may also be administered separately.

A subject to be treated according to the methods described herein (e.g., a subject infected with, a hepatitis B virus) may be one who has been diagnosed by a medical practitioner as having such a condition. Diagnosis may be performed by any suitable means. A subject in whom the development of an infection is being prevented may or may not have received such a diagnosis. One skilled in the art will understand that a subject to be treated according to the present invention may have been identified using standard tests or may have been identified, without examination, as one at high risk due to the presence of one or more risk factors (e.g., exposure to hepatitis B virus, etc.).

Prophylactic treatment may be administered, for example, to a subject not yet exposed to or infected by a hepatitis B virus but who is susceptible to, or otherwise at risk of exposure or infection with an hepatitis B virus.

Therapeutic treatment may be administered, for example, to a subject already exposed to or infected by a hepatitis B who is not yet ill, or showing symptoms or infection, suffering from a disorder in order to improve or stabilize the subject's condition (e.g., a patient already infected with a hepatitis B virus). The result is an improved therapeutic profile. In some instances, as compared with an equivalent untreated control, treatment may ameliorate a disorder or a symptom thereof by, e.g., about 5%, about 10%, about 20%, about 30%, about 40%, about 50%, about 60%, about 70%, about 80%, about 90%, about 95%, or about 100% as measured by any standard technique. In some instances, treating can result in the inhibition of viral replication, a decrease in viral titers or viral load, eradication or clearing of the virus. Therapeutic treatment may be administered, for example, to a subject already exposed to or infected by a hepatitis B who is in the chronic stages of infection (e.g., a patient already infected with a hepatitis B virus). The result is an improved therapeutic profile. In some instances, as compared with an equivalent untreated control, treatment may ameliorate a disorder or a symptom thereof by, e.g., about 5%, about 10%, about 20%, about 30%, about about 40%, about 50%, about 60%, about 70%, about 80%, about 90%, about 95%, or about 100% as measured by any standard technique. In some instances, treating can result in the inhibition of viral replication, a decrease in viral titers or viral load, eradication or clearing of the virus.

In other embodiments, treatment may result in amelioration of one or more symptoms of the infection, including any symptom identified above. According to this embodiment, confirmation of treatment can be assessed by detecting an improvement in or the absence of symptoms.

In other embodiments, treatment may result in reduction or elimination of the ability of the subject to transmit the infection to another, uninfected subject. Confirmation of treatment according to this embodiment is generally assessed using the same methods used to determine amelioration of the disorder, but the reduction in viral titer or viral load necessary to prevent transmission may differ from the reduction in viral titer or viral load necessary to ameliorate the disorder.

In one embodiment, the present invention is a method of inducing an immune response in a subject (e.g., a human) by administering to the subject a recombinant viral vector that encodes at least one gene from a hepatitis B virus. The immune response may be a cellular immune response, a humeral immune response or a combination thereof. The immune response may be a T-cell response, a B-cell response or an antibody response or a combination thereof.

In a particular embodiment, the present invention is a method of inducing an immune response in a subject (e.g., a human) in need thereof by administering to the subject a recombinant viral vector that encodes at least one gene from a hepatitis B virus. The composition may be administered, e.g., by injection (e.g., intramuscular, intraarterial, intravascular, intravenous, intraperitoneal, or subcutaneous).

It will be appreciated that more than one route of administering the vaccines of the present invention may be employed either simultaneously or sequentially (e.g., boosting). In addition, the vaccines of the present invention may be employed in combination with traditional immunization approaches such as employing protein antigens, vaccinia virus and inactivated virus, as vaccines. Thus, in one embodiment, the vaccines of the present invention are administered to a subject (the subject is "primed" with a vaccine of the present invention) and then a traditional vaccine is administered (the subject is "boosted" with a traditional vaccine). In another embodiment, a traditional vaccine is first administered to the subject followed by administration of a vaccine of the present invention. In yet another embodiment, a traditional vaccine and a vaccine of the present invention are co-administered.

It will also be appreciated that single or multiple administrations of the vaccine compositions of the present invention may be carried out. For example, subjects who are particularly susceptible to hepatitis B virus infection may require multiple immunizations to establish and/or maintain protective immune responses. Levels of induced immunity can be monitored by measuring amounts of binding and neutralizing secretory and serum antibodies as well as levels of T cells, and dosages adjusted or vaccinations repeated as necessary to maintain desired levels of protection.

In one embodiment, administration is repeated at least once, at least twice, at least 3 times, at least 4 times, at least 5 times, at least 6 times, at least 7 times, at least 8 times, or more than 8 times.

In one embodiment, administration is repeated once.

In one embodiment, administration is repeated twice.

In one embodiment, about 2-8, about 4-8, or about 6-8 administrations are provided.

In one embodiment, about 1-4-week, 2-4 week, 3-4 week, 1 week, 2 week, 3 week, 4 week or more than 4 week intervals are provided between administrations.

In one specific embodiment, a 4-week interval is used between 2 administrations.

In one specific embodiment, a 4-week interval is used between each administration of 3 total administrations.

In an exemplary treatment strategy, the invention provides a method of treating HBV infection in a subject in need thereof by:
1) administering an effective amount of an antiretroviral or nucleoside analog composition to reduce viral loads;
2) administering an immunogenic composition to prime an immune response to HBV; and
3) administering an immunogenic composition to boost an immune response to HBV to treat one or more symptoms of HBV infection.

In one embodiment, an immune checkpoint inhibitor is administered before the immunogenic composition.

In one embodiment, an immune checkpoint inhibitor is administered concurrently with the immunogenic composition.

In one embodiment, an immune checkpoint inhibitor is administered after the immunogenic composition.

In one embodiment, the immunogenic compositions induces anti-HBV T cell and/or B cell responses.

In one embodiment, the method rescues exhausted T cells and maintains T cell function.

In various embodiments, the methods are continued to obtain select endpoints that are indicative of efficacy of the immunogenic compositions described herein.

In one embodiment, the immunogenic composition is administered to change the HBsAg status of a subject infected with HBV from positive to negative.

In one embodiment, the immunogenic composition is administered to change the status of detectable levels of circulating HBsAg of a subject infected with HBV from positive to negative.

In another embodiment, the immunogenic composition is administered to induce the formation of neutralizing antibodies and antibody-dependent cell-mediated cytotoxicity (ADCC).

In another embodiment, the immunogenic composition is administered to induce $CD4^+$ helper and $CD8^+$ CTL responses.

In another embodiment, the immunogenic composition is administered to reduce or eliminate viral load to undetectable levels and prevent or reduce inflammation in a subject.

A. Dosage

The vaccines are administered in a manner compatible with the dosage formulation, and in such amount, as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $5.0 \times 10^6$ $TCID_{50}$ to about $5.0 \times 10^9$ $TCID_{50}$. The dosage may also depend, without limitation, on the route of administration, the patient's state of health and weight, and the nature of the formulation.

The pharmaceutical compositions of the invention are administered in such an amount as will be therapeutically effective, immunogenic, and/or protective against a pathogenic species of hepatitis B virus. The dosage administered depends on the subject to be treated (e.g., the manner of administration and the age, body weight, capacity of the immune system, and general health of the subject being treated). The composition is administered in an amount to provide a sufficient level of expression that elicits an immune response without undue adverse physiological effects. Preferably, the composition of the invention is a heterologous viral vector that includes one or more polypeptides of the hepatitis B virus, or a nucleic acid molecule encoding one or more genes of the hepatitis B virus, and is administered at a dosage of, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$, more preferably between $1.0 \times 10^6$ and $1.0 \times 10^{10}$ $TCID_{50}$, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). A physician or researcher can decide the appropriate amount and dosage regimen. The composition of the method may include, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$, more preferably between $1.0 \times 10^6$ and $1.0 \times 10^{10}$ $TCID_{50}$, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). The method may include, e.g., administering the composition to the subject two or more times.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., inoculations) are also variable, but are typified by an initial administration followed by subsequent inoculation(s) or other administration(s).

The invention also features a method of inducing an immune response to hepatitis B virus in a subject (e.g., a human) that includes administering to the subject an effective amount of a recombinant viral vector that encodes at least one gene from hepatitis B virus. The subject being treated may not have, but rather be at risk of developing, an infection by a hepatitis B virus. Alternatively, the subject may already be infected with a hepatitis B virus. The composition may be administered, e.g., by injection (e.g., intramuscular, intraarterial, intravascular, intravenous, intraperitoneal, or subcutaneous).

The term "effective amount" is meant the amount of a composition administered to improve, inhibit, or ameliorate a condition of a subject, or a symptom of a disorder, in a clinically relevant manner (e.g., improve, inhibit, or ameliorate infection by hepatitis B virus or provide an effective immune response to infection by hepatitis B virus). Any improvement in the subject is considered sufficient to achieve treatment. Preferably, an amount sufficient to treat is an amount that prevents the occurrence or one or more symptoms of hepatitis B virus infection or is an amount that reduces the severity of, or the length of time during which a subject suffers from, one or more symptoms of hepatitis B virus infection (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of the pharmaceutical composition used to practice the methods described herein (e.g., the treatment of hepatitis B virus infection) varies depending upon the manner of administration and the age, body weight, and general health of the subject being treated.

Ultimately, the prescribers or researchers will decide the appropriate amount and dosage. It is important to note that the value of the present invention may never be demonstrated in terms of actual clinical benefit. Instead, it is likely that the value of the invention will be demonstrated in terms of success against a surrogate marker for protection. For an indication such as hepatitis B virus infection, in which it is impractical or unethical to attempt to measure clinical benefit of an intervention, the FDA's Accelerated Approval process allows approval of a new vaccine based on efficacy against a surrogate endpoint. Therefore, the value of the invention may lie in its ability to induce an immune response that constitutes a surrogate marker for protection.

Similarly, FDA may allow approval of vaccines against hepatitis B virus based on its Animal Rule. In this case, approval is achieved based on efficacy in animals. The value of the invention may lie in its ability to protect relevant animal species against infection with hepatitis B virus, thus providing adequate evidence to justify its approval.

The composition of the method may include, e.g., between $1.0\times10^4$ and $9.9\times10^{12}$ TCID$_{50}$ of the viral vector, preferably between $1.0\times10^5$ TCID$_{50}$ and $1.0\times10^{11}$ TCID$_{50}$, more preferably between $1.0\times10^6$ and $1.0\times10^{10}$ TCID$_{50}$, or most preferably between $5.0\times10^6$ and $5.0\times10^9$ TCID$_{50}$. The composition may include, e.g., at least $5.0\times10^6$ TCID$_{50}$ of the viral vector. The method may include, e.g., administering the composition two or more times. In some instances, it may be desirable to combine the hepatitis B virus vaccines of the present invention with vaccines, which induce protective responses to other agents, particularly other viruses. For example, the vaccine compositions of the present invention can be administered simultaneously, separately or sequentially with other genetic immunization vaccines such as those for influenza (Ulmer, J. B. et al., Science 259:1745-1749 (1993); Raz, E. et al., PNAS (USA) 91:9519-9523 (1994)), malaria (Doolan, D. L. et al., J. Exp. Med. 183: 1739-1746 (1996); Sedegah, M. et al., PNAS (USA) 91:9866-9870 (1994)), and tuberculosis (Tascon, R. C. et al., Nat. Med. 2:888-892 (1996)).

B. Administration Routes

As used herein, the term "administering" refers to a method of giving a dosage of a pharmaceutical composition of the invention to a subject. The compositions utilized in the methods described herein can be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, intraarterial, intravascular, and intramuscular administration. The preferred method of administration can vary depending on various factors (e.g., the components of the composition being administered and the severity of the condition being treated).

Administration of the pharmaceutical compositions (e.g., vaccines) of the present invention can be by any of the routes known to one of skill in the art. Administration may be by, e.g., intramuscular injection. The compositions utilized in the methods described herein can also be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. The preferred method of administration can vary depending on various factors, e.g., the components of the composition being administered and the severity of the condition being treated.

In addition, single or multiple administrations of the compositions of the present invention may be given to a subject. For example, subjects who are particularly susceptible to hepatitis B virus infection may require multiple administrations to establish and/or maintain protection against the virus. Levels of induced immunity provided by the pharmaceutical compositions described herein can be monitored by, e.g., measuring amounts of neutralizing secretory and serum antibodies. The dosages may then be adjusted or repeated as necessary to maintain desired levels of protection against viral infection.

The claimed invention is further described by way of the following non-limiting examples. Further aspects and embodiments of the present invention will be apparent to those of ordinary skill in the art, in view of the above disclosure and following experimental exemplification, included by way of illustration and not limitation, and with reference to the attached figures.

EXAMPLES

Example 1: Construction of a Virus-Like Particle Vaccines for Hepatitis B Virus Antigens This example provides information on exemplary MVA vaccine vectors. Table 1 lists two exemplary MVA vaccine vectors.

TABLE 1

| MVA vaccine vectors | | |
|---|---|---|
| Vaccine designation | Structural sequence | Non-Structural sequence |
| GEO-HBV01 | PreS2_S | PreCore/Core + Truncated X |
| GEO-HBV02 | PreS.HA | M1.P41A |

For GEO0HBV01, the preS2_S sequence was cloned into pLW-73 MVA shuttle vector, placed under the control of vaccinia virus mH5 promoter. The pLW73-preS2_S shuttle vector is used to insert the HBV preS2_S sequences between essential genes I8R and G1L. The PreCore/Core-tr.X sequences were cloned into IPW-76 MVA shuttle vector. PreCore/Core is placed under the control of vacinia virus mH5 promoter and the truncated X (tr.X) gene is under the control of vaccinia virus P7.5 promoter. The pLW76 Pre-Core/Core-tr.X shuttle vector has been used to insert the HBV preCore/Core and tr.X sequences into the modified deletion III site of MVA (between the AS0R and B1R genes).

For GEO-HBV02, the preS.HA sequence was cloned into pLW-73 MVA shuttle vector, placed under the control of vaccinia virus mH5 promoter. The pLW73-preS.HA shuttle vector is used to insert the HBV preS.HA sequences between essential genes I8R and G1L. The M1.P41A sequences were cloned into IPW-76 MVA shuttle vector. M1.P41A is placed under the control of vacinia virus mH5 promoter. The pLW76 M1.P41A shuttle vector has been used to insert the HBV M1.P41A sequence into the modified deletion Ill site of MVA (between the A50R and B1R genes).

Example 2: Evaluation of Virus-Like Particle Vaccines of the Hepatitis B Virus Antigens for Protection Protects Mice Against Challenge The immunogenicity of HBV antigen VLP is assessed as a potential vaccine candidate. Immunization with VLP MVA vaccine is evaluated for induction both potent humeral and cellular immune responses, and protection from HBV challenge.

Materials and Methods

Plasmids and Cells

The vectors for expressing HBV preS2_S or PreS.HA are described herein. 293T cells are maintained in DMEM supplemented with 10% fetal bovine serum (FBS).

Indirect Immunofluorescence 293T cells are grown on glass coverslips and transfected with pGEO-HBV01 and pGEO-HBV02 and 48 hr posttransfection, cells are fixed with 4% paraformaldehyde.

Cells are classified into two groups. One was permeabilized with 0.2% Triton X-100 for 5 min, the other without permeabilization. After blocking for 1 h in PBS containing 5% goat serum, all cells are incubated with poly clonal rabbit anti-preS sera at 4° C. overnight. Cells are washed with PBS following incubation with Alexa Fluor® 488-Conjugated goat anti-rabbit secondary antibody for 1 h at 37° C. After washing, cells are stained with DAPI for 10 min, and then mounted onto microscope slides. Confocal slices are acquired with a 100× objective, using a Zeiss 510 confocal microscope with random sampling.

Preparation and Characterization of the Virus-Like Particles

The pGEO-HBV01 and pGEO-HBV02 plasmids are transfected into 293T cells with polyethylenimine. 72 hr after transfection, the culture medium is centrifuged at 6000 rpm for 15 min at 4° C. to remove cellular debris, followed by centrifugation at 22,000 rpm for 3 hr at 4° C. The pellet is resuspended in PBS at 4° C. overnight, and further purified through a 20%-60% sucrose gradient in a Beckman SW41 Ti rotor at 30,000 rpm for 3 hr at 4° C. The 40% sucrose fraction is harvested and diluted with PBS by about 5 fold. After centrifugation at 22,000 rpm for 3 hr at 4° C. to remove the sucrose, the virus-like particles are resuspended in PBS at 4° C. overnight. A sample is applied to a 400 mesh carbon-coated copper grid, and stained with 1% phosphotungstic acid (J&K Scientific). HBV antigenVLP are visualized on a Tecnai cJ2 Spirit transmission election microscope operating at 120 kV.

LC-MSIMS Analysis

The expression of antigens is analyzed by LC-MS/MS. Briefly, 40% sucrose fraction are subjected to electrophoresis on a 12%-SDS-PAGE gel, which is stained by coomassie R250. The coomassie R250 stained gel bands are cut, followed by in-gel digestion with trypsin [promega, enzyme: protein=1:50 (wt/wt)] at 37° C. for 12 h in 25 mM ammonium bicarbonate buffer. The lyophilized tryptic digested samples are re-dissolved in 2% acetonitrile, 0.1% formic acid, and loaded on ChromXP C18 (3 !Im, 120 A) nanoLC trap column. The online trapping, desalting procedure is carried out at a flow rate of 2 !iL/min for 10 min with 100% solvent A (Solvent A: water/acetonitrile/formic acid=9812/0.1% solvent B: 2/98/0.1%). Then, an 60-min gradient elution ranging from 5-35% acetonitrile (0.1% formic acid) is used on an analytical column (75 !lm×15 cm C18-3 !lm 120 A, ChromXP Eksigent). LC-MS/MS analysis is performed with a Triple TOF 5600 System (AB SCIEX, Concord, ON) fitted with a Nanospray III source (AB SCIEX, Concord, ON). Data is acquired using an ion spray voltage of 2.5 kV, curtain gas of 30 PSI, nebulizer gas of 5 PSI, and an interface heater temperature of 150° C. The MS is operated with TOF-MS scans. For IDA, survey scans were acquired in 250 ms and as many as 25 product ion scans (90 ms) are collected if exceeding a threshold of 150 counts per second (counts/s) and with a +2 to +4 charge-state. A Rolling collision energy setting is applied to all precursor ions for collision-induced dissociation. Dynamic exclusion was set for Yz of peak width (~12 s). For data analysis, the .wiff files are processed by ProteinPilot 5.0. Searches are performed against the local database including the protein sequences for the HBV antigens using the default settings.

Immunization and Challenge

Female Balb/c mice of 6-8 weeks old are immunized by injecting the MVA vector in the hindlimb. A booster is given on day 22. Blood was collected on day 52, and 112, and neutralizing antibody titers were determined by ELISA. On day 52, activated T cells in splenocytes or intrahepatic leukocytes are analyzed by ELISPOT and FACS. The immunized mice are challenged on day 70. 10 !lg of pT-HBV1.3 (a plasmid containing 1.3 genome length of HBV) is in hydrodynamic injection to establish HBV infection as previously described (Yang P L, et al. Proc Nat! Acad Sci USA 2002 99: 13825-13830). Blood samples are collected at different time points to measure HBV antigens. On day 67, mice are sacrificed and liver tissues are used for measuring antigens and RNA of HBV. Activated T cells are also analyzed by FACS and ELISPOT assay. All mouse experiments are conducted in accordance with the institutional guidelines following the experimental protocol reviewed and approved by university animal control authority.

Isolation of Splenocytes and Intrahepatic Leukocytes

For the isolation of splenocytes, splenocytes are gently grinded followed by passaging through 40 um strainers and treating with ACK lysing buffer. After washing with PBS, cells were resuspended in DMEM supplemented with 10% fetal bovine serum (FBS) and 1% Penicillin-Streptomycin-L-Glutamine. For the isolation of intrahepatic leukocytes, mice livers are perfused with pre-warmed Hanks' balanced solution without Ca2+, Mg2+, followed by perfusing with 20 ml 0.025% collagenase D in Hanks' balanced salt solution, and let sit for 10 min at 37° C. Livers are then gently grinded followed by passaging through 40 !-lm strainers. After centrifugation, cells are resuspended in 40% (vol/vol) Percell in DMEM, and layered over 70% Percell in PBS (vol/vol). After centrifugation of the gradient for 20 min at 2000 rpm, the cells at the interphase are collected. The cells are then treated with ACK lysing buffer, washed with PBS, and resuspended in DMEM supplemented with 10% fetal bovine serum (FBS) and 1% Penicillin-Streptomycin-L-Glutamine for further analysis.

Enzyme-Linked Immunospot Assay

T cell responses are determined using an IFN-γ ELISPOT set (BO Biosciences) following the manufacturer's protocol. Briefly, 96-well plates are coated with purified anti-mouse IFN−/, antibody (1:200) at 4° C. overnight, and then are blocked for 2 h using DMEM supplemented with 10% fetal bovine serum (FBS) and 1% PenicillinStreptomycin-L-Glutamine. Splenocytes or intrahepatic leukocytes are seeded at 2×IO5/well. Peptides representing previously described epitopes present in protein or purified protein are used to stimulate cells for 36 h at 37° C. in a 5% CO2 and humidified incubator, with media and phorbol myristate acetate (PMA)/ionomycin-30 treated cells used as negative and positive controls, respectively. After being washed, cells are incubated with biotinylated anti-mouse IFN-γ antibody (1:250) for 2 hat room temperature, and then incubated with streptavidin-horseradish peroxidase (HRP) (1:1,000) for 1 h. Following the final washes, 3-amino-9-ethylcarbazole (AEC) substrate (Alfa Aesar) is added to the wells and allowed to develop at room temperature for 40 min. The reaction is stopped with distilled water, and the plates are allowed to air dry 5 before spot-forming cells are enumerated by using an ELISPOT plate reader.

Flow Cytometry

Splenocytes or intrahepatic leukocytes are resuspended in DMEM supplemented with 10% fetal bovine serum and 1% Penicillin-Streptomycin-L-Glutamine, and then are seeded at 2×10$^6$/well. The cells are then stimulated for 6 h with preS-specific peptides or purified recombinant preS diluted to a final concentration of 10 llg/ml in DMEM supplemented with 211 g/ml brefeldin A (BD Biosciences). The cells were then washed in staining buffer (pBS containing 2% fetal bovine serum) and stained for CD8 and CD4 surface expression for 30 min at 4° C. using fluorescein isothiocyanate (FITC) conjugated anti-mouse CD8 antibody (BD Biosciences) and peridinin chlorophyll protein (perCP)-conjugated anti-mouse CD4 antibody (BD Biosciences). Then the cells are washed, fixed, and permeabilized using a commercially available Cytofix/Cytoperm kit (BD Biosciences). The cells are then stained for 40 min at 4° C. for intracellular cytokine expression using phycoerythrin (PE)-conjugated anti-mouse IFN-r antibody (BD Biosciences). After washing, cells are resuspended in staining buffer and analyzed using a BD FACS Canto™ II flow cytometer (BD Biosciences) and FACSDiva Version.

ELISA

Purified antigen (5 flg/ml) or preS VLP (1 flg/ml) is absorbed to 96 well plates, blocked with 10% BSA, and then 50 fll of 1:100 dilution of sera is incubated for 30 min at 37° C. followed by incubation with added HRP-conjugated anti-mouse lgG, 5 lgG1 or lgG2a (Santa Cruz Biotechnology) for 30 min at 37° C., and then with TMB substrate for 10 minutes before stopping with 2 M H2S04 for measurement of optical density at 450 nm. In addition, serum samples were diluted 1:5 for HBsAg ang HBeAg detection.

Immunohistochemistry

Liver tissue is collected and fixed in 10% neutral formalin. After paraffin embedding, liver sections are used to detect HBV core antigen by immunohistochemical staining using polyclonal rabbit anti-HBcAg antibody (Dako).

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference in their entirety.

We claim:

1. A modified vaccinia Ankara (MVA) vector comprising a first nucleic acid sequence and a second nucleic acid sequence, wherein:
   the first nucleic acid sequence encodes a hepatitis B virus structural protein comprising a PreS2-S protein, wherein the first nucleic acid sequence is inserted into the MVA vector under the control of at least one promoter compatible with a poxvirus expression system;
   the second nucleic acid sequence encodes hepatitis B non-structural proteins PreCore/Core and Truncated X; wherein the second nucleic acid sequence is inserted into the MVA vector under the control of at least one promoter compatible with a poxvirus expression system; and,
   wherein the hepatitis B virus structural protein and hepatitis B non-structural proteins assemble into virus-like particles (VLPs) when expressed.

2. The modified vaccinia Ankara (MVA) vector of claim 1, wherein the first nucleic acid sequence is inserted between MVA genes I8R and G1L.

3. The modified vaccinia Ankara (MVA) vector of claim 1, wherein the first nucleic acid sequence is inserted between MVA genes I8R and G1L, and the second nucleic acid sequence is inserted in modified deletion III.

4. The modified vaccinia Ankara (MVA) vector of claim 1, wherein the promotor is selected from the group consisting of Pm2H5, Psyn II, mH5, P7.5 promoters, and a combination thereof.

5. The modified vaccinia Ankara (MVA) vector of claim 1, wherein the first nucleic acid sequence comprises SEQ ID NO: 1.

6. The modified vaccinia Ankara (MVA) vector of claim 1, wherein the second nucleic acid sequence comprises SEQ ID NO: 2 and SEQ ID NO: 3.

7. The modified vaccinia Ankara (MVA) vector of claim 1, wherein the first nucleic acid sequence comprises SEQ ID NO: 1 and the second nucleic acid sequence comprises SEQ ID NO: 2 and SEQ ID NO: 3.

8. A pharmaceutical composition comprising the modified vaccinia Ankara (MVA) vector of claim 1, and a pharmaceutically acceptable carrier.

9. A method for generating an immune response in a human to hepatitis B virus comprising administering to the human an effective amount of a pharmaceutical composition comprising a modified vaccinia Ankara (MVA) vector and a pharmaceutically acceptable carrier, wherein the MVA vector comprising a first nucleic acid sequence and a second nucleic acid sequence, wherein:

the first nucleic acid sequence encodes a hepatitis B virus structural protein comprising a PreS2-S protein, wherein the first nucleic acid sequence is inserted into the MVA vector under the control of at least one promoter compatible with a poxvirus expression system;

the second nucleic acid sequence encodes hepatitis B non-structural proteins PreCore/Core and Truncated X;

wherein the second nucleic acid sequence is inserted into the MVA vector under the control of at least one promoter compatible with a poxvirus expression system; and, wherein the hepatitis B virus structural protein and hepatitis B non-structural proteins assemble into virus-like particles (VLPs) when expressed in the human.

10. The method of claim 9, wherein the first nucleic acid sequence is inserted between MVA genes I8R and G1L.

11. The method of claim 9, wherein the first nucleic acid sequence is inserted between MVA genes I8R and G1L, and the second nucleic acid sequence is inserted in modified deletion III.

12. The method of claim 9, wherein the promotor is selected from the group consisting of Pm2H5, Psyn II, mH5, P7.5 promoters, and a combination thereof.

13. The method of claim 9, wherein the first nucleic acid sequence comprises SEQ ID NO: 1.

14. The method of claim 9, wherein the second nucleic acid sequence comprises SEQ ID NO: 2 and SEQ ID NO: 3.

15. The method of claim 9, wherein the first nucleic acid sequence comprises SEQ ID NO: 1 and the second nucleic acid sequence comprises SEQ ID NO: 2 and SEQ ID NO: 3.

* * * * *